United States Patent
Arai et al.

(10) Patent No.: US 8,657,811 B2
(45) Date of Patent: Feb. 25, 2014

(54) INTRAVASCULAR DIAGNOSTIC OR THERAPEUTIC APPARATUS USING HIGH-INTENSITY PULSED LIGHT

(75) Inventors: Tsunenori Arai, Kanagawa (JP); Eriko Suga, Kanagawa (JP); Erika Yamashita, Kanagawa (JP); Hikaru Futami, Kanagawa (JP)

(73) Assignee: Keio University, Tokyo (JP)

( * ) Notice: Subject to any disclaimer, the term of this patent is extended or adjusted under 35 U.S.C. 154(b) by 1551 days.

(21) Appl. No.: 10/554,871

(22) PCT Filed: May 6, 2004

(86) PCT No.: PCT/JP2004/006407
§ 371 (c)(1),
(2), (4) Date: Feb. 10, 2008

(87) PCT Pub. No.: WO2005/063113
PCT Pub. Date: Jul. 14, 2005

(65) Prior Publication Data
US 2008/0221560 A1 Sep. 11, 2008

(30) Foreign Application Priority Data

May 1, 2003 (JP) .................................. 2003-126633
Sep. 19, 2003 (JP) .................................. 2003-328984

(51) Int. Cl.
*A61B 18/20* (2006.01)
(52) U.S. Cl.
USPC .................................. 606/14; 128/898; 607/89
(58) Field of Classification Search
USPC .................... 606/2–19; 600/476; 128/898; 607/88–92
See application file for complete search history.

(56) References Cited

U.S. PATENT DOCUMENTS

| 4,576,146 A | | 3/1986 | Kawazoe et al. |
| 4,641,650 A | * | 2/1987 | Mok .............................. 606/12 |
| 4,768,858 A | * | 9/1988 | Hussein ....................... 385/118 |
| 4,784,132 A | * | 11/1988 | Fox et al. ....................... 606/15 |
| 4,869,246 A | | 9/1989 | Adair |
| 4,887,605 A | * | 12/1989 | Angelsen et al. ............. 600/439 |
| 4,920,413 A | | 4/1990 | Nakamura et al. |
| 5,066,291 A | * | 11/1991 | Stewart ............................ 606/3 |

(Continued)

FOREIGN PATENT DOCUMENTS

| JP | 59-172621 A | 9/1984 |
| JP | 2-4389 A | 1/1990 |

(Continued)

OTHER PUBLICATIONS

Supplementary European Search Report EP 04 73 1487 dated Jun. 10, 2010.

(Continued)

*Primary Examiner* — Bill Thomson
*Assistant Examiner* — Jeffrey Lipitz
(74) *Attorney, Agent, or Firm* — Foley & Lardner LLP

(57) ABSTRACT

An intravascular diagnostic or therapeutic apparatus capable of removing blood in an intravascular lumen to be observed using a minimally invasive method is provided. The apparatus includes high-intensity pulsed light generating means and high-intensity pulsed light transmitting means for transmitting high-intensity pulsed light, capable of irradiating the interior of a blood vessel with high-intensity pulsed light, producing water-vapor bubbles and temporarily removing the blood in the blood vessel.

38 Claims, 15 Drawing Sheets
(7 of 15 Drawing Sheet(s) Filed in Color)

(56) References Cited

U.S. PATENT DOCUMENTS

| | | | |
|---|---|---|---|
| 5,178,616 A | * | 1/1993 | Uemiya et al. .................... 606/7 |
| 5,632,739 A | * | 5/1997 | Anderson et al. ................. 606/2 |
| 5,725,522 A | * | 3/1998 | Sinofsky ............................ 606/8 |
| 6,048,349 A | * | 4/2000 | Winston et al. ............... 606/108 |
| 6,428,531 B1 | * | 8/2002 | Visuri et al. ...................... 606/7 |

FOREIGN PATENT DOCUMENTS

| | | |
|---|---|---|
| JP | 2-28926 A | 11/1990 |
| WO | WO 99/16366 | 4/1999 |
| WO | WO 00/33913 | 6/2000 |

OTHER PUBLICATIONS

E. Duco Jansen PhD et al., "Effect of Pulse Duration on Bubble Formation and Laser-Induced Pressure Waves During Holmium Laser Ablation", Lasers in Surgery and Medicine, 18:278-293 (1996).

Tom G. Van Leeuwen et al., "Noncontact Tissue Ablation by Holmium: YSGG Laser Pulses in Blood", Lasers in Surgery and Medicine 11:26-34 (1991).

Ralf Brinkmann et al., "Single-Pulse 30-J Holmium Laser for Myocardial Revascularization—A Study on Ablation Dynamics in Comparison to $CO_2$ Laser—TMR", IEEE Journal of Selected Topics in Quantum Electronics, vol. 5, No. 4, Jul./Aug. 1999, pp. 969-980.

\* cited by examiner

Fig. 12
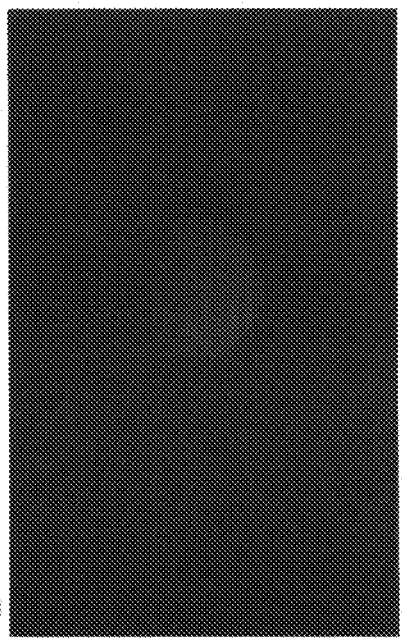
LASER INTENSITY 200 mJ/pulse
DELAY TIME 140μS
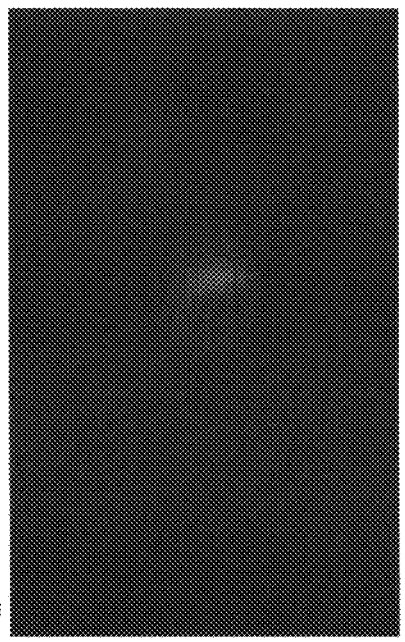
LASER INTENSITY 450 mJ/pulse
DELAY TIME 140μS
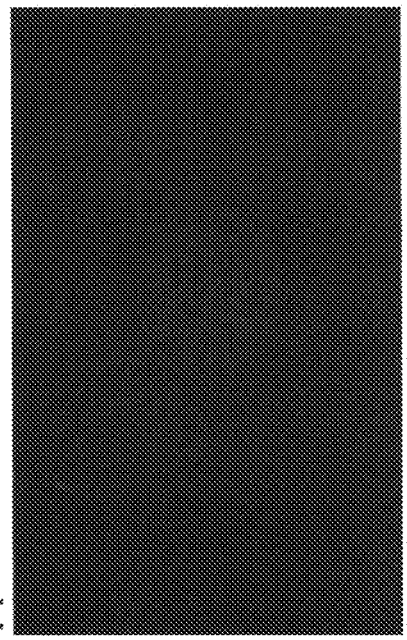
NO LASER IRRADIATION
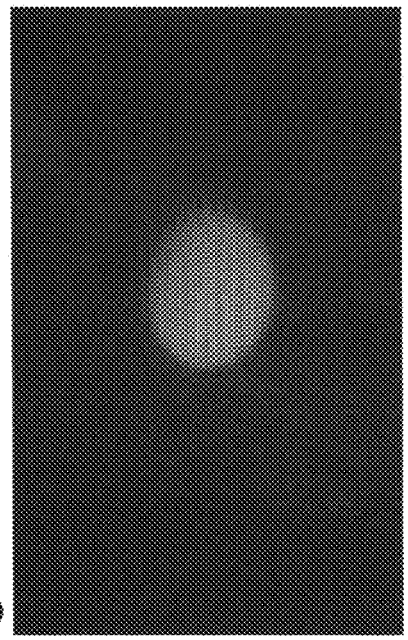
CONTROL IN AIR

INTRAVASCULAR DIAGNOSTIC OR THERAPEUTIC APPARATUS USING HIGH-INTENSITY PULSED LIGHT

TECHNICAL FIELD

The present invention relates to an intravascular diagnostic or therapeutic apparatus provided with high-intensity pulsed light irradiating means such as pulsed laser, which irradiates blood with the high-intensity pulsed light and generates water-vapor bubbles to enable diagnostics and therapy of an intravascular lumen. An example of such an apparatus is an angioscope which allows an observation of an intravascular lumen.

BACKGROUND ART

Conventionally, intravascular diagnostic or therapy has been conducted by inserting a catheter into a blood vessel using light for diagnostics or therapy. For example, a vessel lumen has been observed with an angioscope by irradiating illumination light. Furthermore, angioplasty or the like has been conducted by irradiating a vessel lumen with high-intensity pulsed light such as laser light. However, when light is irradiated into the blood vessel while blood exists in the blood vessel, light having a wavelength of visible light to ultraviolet light is absorbed by hemoglobin in the blood and infrared light is absorbed by water. For this reason, it has been difficult to allow light to reach the region of the blood vessel targeted for diagnostics or therapy. Therefore, there has been conventionally a necessity for use of a balloon such as a blood flow shut-off balloon to shut off a blood flow for intravascular diagnostics or therapy or for contact irradiation by causing the region to be irradiated with light for diagnostics or therapy to contact the region of the blood vessel having disease or trouble. For example, when an intravascular lumen is optically observed, it is necessary to remove blood inside the blood vessel which obstacles the field of view in the region observed, and therefore the blood flow is temporarily stopped using a shut-off balloon or by injecting a transparent fluid such as saline with heparin into a region to be observed in the blood vessel and replacing the blood in the region to be observed with the transparent saline or the like (see Patent Document 1 and Patent Document 2).

However, when the blood flow is stopped using the shut-off balloon, a hemostasis time for avoiding ischemia is limited and it is not possible to secure a sufficient time for diagnostics or therapy. Use of the balloon cannot completely shut off the blood flow, either.

Furthermore, contact irradiation of light also requires special means for causing an irradiation section to contact the intravascular lumen wall and needs to avoid excessive contact so as not to damage the blood vessel wall.

Moreover, when the field of view is secured by removing the blood in saline using a conventional angioscope, even a small amount of blood is mixed in, illumination light is diffused and reflected, which obstructs the field of view considerably. This causes a vicious cycle of requiring further injection of a large amount of saline.

Furthermore, these conventional methods stop a blood flow or inject a large amount of foreign matters into the blood vessel, blocking the circulation of blood, which is an oxygen carrier, preventing a sufficient amount of oxygen from being supplied to peripherals and thus presenting a high level of invasiveness against an examinee. The influence of the exclusion of blood in the coronary artery is particularly large and it is necessary to practice the conventional methods within a limited time while always monitoring ischemia with an electrocardiogram, and in this way, operation of the coronary artery endoscope involves many difficulties.

On the other hand, a method of observing a state of intravascular lumen using ultrasound (Intravascular Ultrasound: IVUS) instead of light is also being widely practiced. While this method is minimally invasive, it is not a method intended to directly observe an intravascular lumen and it is unable to obtain information on color tone, and it is difficult to provide precise characteristic diagnostics of lesioned parts. Especially in the case of a coronary artery disease, it has been impossible to distinguish yellow atheroma which provokes acute transmural myocardial infarction due to intimal breakdown from white atheroma in which fibrosing advances without producing intimal breakdown.

As shown above, the conventional methods cannot provide any precise and safe diagnostics or therapy on a coronary artery lumen in particular.

Patent Document 1 JP Patent Publication (Kokai) No. 6-296695 A

Patent Document 2 JP Patent Publication (Kokai) No. 11-262528 A

DISCLOSURE OF THE INVENTION

It is an object of the present invention to provide an intravascular diagnostic or therapeutic apparatus capable of removing blood in an intravascular lumen to be observed using a minimally invasive method. More specifically, the present invention is intended to provide a minimally invasive intravascular diagnostic or therapeutic apparatus which allows observation or therapy of the intravascular lumen by irradiating the intravascular lumen with high-intensity pulsed light such as pulsed laser, generating water-vapor bubbles in the blood vessel filled with blood observed in an extremely short time, removing the blood in the region and irradiating the region with light for diagnostics or therapy.

The present inventors have made every effort to solve the problems with the conventional intravascular diagnostic or therapeutic apparatus and develop an intravascular diagnostic or therapeutic apparatus capable of providing minimally invasive, efficient diagnostic or therapeutic effects, for example, an angioscope capable of obtaining a minimally invasive, clear image. The present inventors have come to complete the present invention by noticing a phenomenon that when high-intensity pulsed light is irradiated into a capillary containing water, the water vaporizes by absorbing energy of irradiation of high-intensity pulsed light, producing water-vapor bubbles, and discovering the fact that water-vapor bubbles are generated in the blood in the blood vessel when high-intensity pulsed light is irradiated in the blood vessel, the blood is temporarily removed and irradiating light for diagnostics or therapy at that moment prevents light from being absorbed by the blood, allows light to reach the intravascular lumen wall, thus making it possible to conduct diagnostics or therapy in the intravascular lumen. For example, an angioscope, one of apparatuses of the present invention, allows the intravascular lumen to be observed easily.

That is, the present invention will be summarized as follows:

[1] An intravascular diagnostic or therapeutic apparatus provided with high-intensity pulsed light generating means and high-intensity pulsed light transmitting means for transmitting high-intensity pulsed light, capable of irradiating high-intensity pulsed light into blood vessel, generating water-vapor bubbles and temporarily removing blood in blood vessel

[2] The intravascular diagnostic or therapeutic apparatus in [1] which has the form of a catheter, provided with pulsed light irradiating means for irradiating light for diagnostics or therapy into blood vessel, enabling diagnostics or therapy in intravascular lumen

[3] The intravascular diagnostic or therapeutic apparatus in [2], wherein pulsed light for diagnostics or therapy is ultraviolet light, visible light, near-infrared light or infrared light

[4] The intravascular diagnostic or therapeutic apparatus in [3], wherein pulsed light for diagnostics or therapy is ultraviolet light and relaxes blood vessel

[5] The intravascular diagnostic or therapeutic apparatus in [3], wherein pulsed light for diagnostics or therapy is ultraviolet light, visible light, near-infrared light or infrared light and contracts blood vessel

[6] The intravascular diagnostic or therapeutic apparatus in [2], wherein pulsed light for diagnostics or therapy has high intensity

[7] The intravascular diagnostic or therapeutic apparatus in [2], wherein pulsed light for diagnostics or therapy can destroy atheroma of arterial sclerosis in blood vessel or thrombus in blood vessel

[8] The intravascular diagnostic or therapeutic apparatus in [2], wherein pulsed light for diagnostics or therapy is selectable from a group of light generated by solid laser, semiconductor laser, dye laser, variable wavelength near-infrared laser, optical parametric oscillator (OPO), Raman laser, light generated by coupling these lasers with non-linear optical converter and flash lamp

[9] The intravascular diagnostic or therapeutic apparatus in [8], wherein pulsed light for diagnostics or therapy is used for photochemical therapy

[10] Furthermore, the diagnostic or therapeutic apparatus in catheter form in any one of [1] to [3] and [8], which is an angioscope, having the form of a catheter, provided with illumination light irradiating means for pulsed-illuminating the interior of blood vessel to enable optical observation and image-pickup means for taking images of intravascular lumen illuminated with illumination light

[11] The angioscope in [10], further provided with solution feeding means, capable of replacing blood in a local region irradiated with high-intensity pulsed light with a liquid whose high-intensity pulsed light absorbability is close to that of water

[12] The intravascular diagnostic or therapeutic apparatus in any one of [1] to [11], wherein an absorbing coefficient of water ranges from 10 to 1000 $cm^{-1}$ with wavelength of high-intensity pulsed light

[13] The intravascular diagnostic or therapeutic apparatus in any one of [1] to [12], which is an angioscope, wherein wavelength of high-intensity pulsed light ranges from 0.3 to 3 μm

[14] The intravascular diagnostic or therapeutic apparatus in [13], which is an angioscope, wherein wavelength of high-intensity pulsed light ranges from 1.5 to 2.5 μm

[15] The intravascular diagnostic or therapeutic apparatus in any one of [1] to [14], which is an angioscope, wherein high-intensity pulsed light is pulsed laser

[16] The intravascular diagnostic or therapeutic apparatus in any one of [1] to [15], wherein high-intensity pulsed light is pulsed light generated by an optical parametric oscillator (OPO)

[17] The intravascular diagnostic or therapeutic apparatus in [15], wherein the laser is a solid laser using rare-earth ions

[18] The intravascular diagnostic or therapeutic apparatus in [17], wherein laser medium is Ho or Tm and laser base material is selected from a group of YAG, YLF, YSGG and YVO

[19] The intravascular diagnostic or therapeutic apparatus in [18], wherein laser is Ho:YAG laser or Tm:YAG laser

[20] The intravascular diagnostic or therapeutic apparatus in any one of [1] to [19], wherein pulse width of irradiation of high-intensity pulsed light is 10 ns to 10 ms

[21] The intravascular diagnostic or therapeutic apparatus in [20], wherein pulse width of irradiation of high-intensity pulsed light is 100 μs to 400 μs

[22] The intravascular diagnostic or therapeutic apparatus in any one of [1] to [21], wherein a delay is provided between irradiation of pulsed light for diagnostics or therapy and irradiation of high-intensity pulsed light

[23] The intravascular diagnostic or therapeutic apparatus in any one of [1] to [22], wherein irradiation timing of high-intensity pulsed light and pulsed light for diagnostics or therapy is delayed from or synchronized with a pulsating blood flow using an electrocardiograph and high-intensity pulsed light can be irradiated when the pulsating blood flow decreases

[24] The intravascular diagnostic or therapeutic apparatus in any one of [1] to [23] having irradiation field operability

[25] The angioscope in any one of [1] to [24], which is a cardioscope

[26] The intravascular diagnostic or therapeutic apparatus in any one of [10] to [25], which is an angioscope, further provided with diagnostic or therapeutic means

[27] The intravascular diagnostic or therapeutic apparatus in [26], which is an angioscope, capable of obtaining images of the interior of blood vessel as moving images by repeating irradiation of high-intensity pulsed light and pulsed illumination at short intervals, discovering lesioned part in blood vessel while observing the images or conducting diagnostics or therapy inside blood vessel using diagnostic or therapeutic means

[28] The intravascular diagnostic or therapeutic apparatus in [26] or [27], which is an angioscope, wherein the diagnostic or therapeutic means is selectable from a group of directional atherectomy apparatus, thrombus aspirator, rotablator and apparatus for biopsy The present specification includes contents described in the specification and/or drawings of Japanese Patent Applications No. 2003-126633 and 2003-328984, which form the basis of priority of the present application.

BRIEF DESCRIPTION OF THE DRAWINGS

The application contains at least one drawing executed in color. Copies of this patent or patent application publication with color drawing(s) will be provided by the Office upon request and payment of the necessary fee.

FIG. 12 shows photos when a silicon tube is filled with milk and the interior of the tube is observed with a delay time 140 μs;

DESCRIPTION OF SYMBOLS

Figure 1:
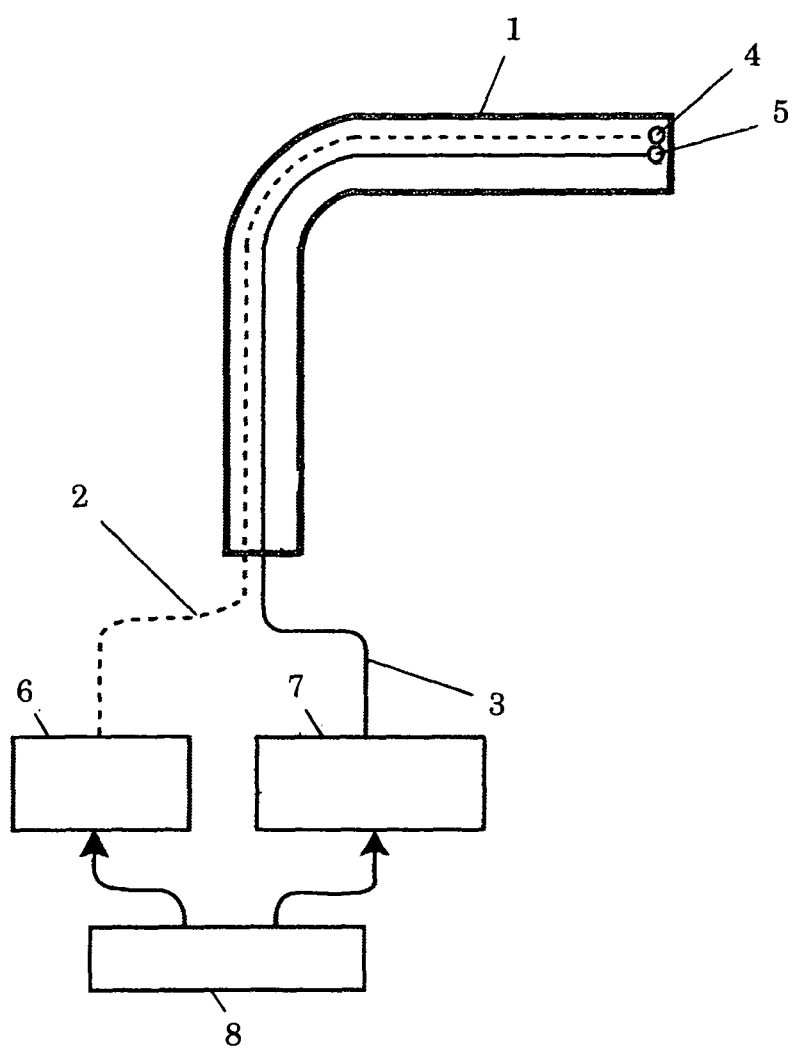
FIG. 1 illustrates an intravascular diagnostic or therapeutic apparatus according to the present invention.

1, catheter
2, high-intensity pulsed light transmitting fiber
3, light transmitting fiber for diagnostics or therapy
4, high-intensity pulsed light irradiation section
5, light irradiation section for diagnostics or therapy
6, high-intensity pulsed light source
7, light source of light for diagnostics or therapy
8, delay pulse generator
9, illumination section
10, lightguide (for illumination)
11, pulse illumination light source
12, observation section
13, image guide
14, image pickup device
15, processing section
16, monitor
17, lumen (saline injection)
18, catheter sheath
19, laser transmission fiber
20, image guide
21, lightguide
22, small-diameter endoscope
23, sheath
24, Ho:YAG laser generator
25, flash lamp
26, condenser lens
27, delay generator
28, CCD camera
29, monitor
30, porcine coronary arteries Best Mode for Carrying Out the Invention Examples of the present invention will be explained in detail below.

The present invention is an intravascular diagnostic or therapeutic apparatus using a phenomenon that when a high-intensity pulsed light of a pulsed laser or the like is irradiated in a blood vessel, the water in the blood absorbs the energy of the high-intensity pulsed light, vaporizes and produces water-vapor bubbles (bubbles induced by high-intensity pulsed light) and the blood in that area is temporarily removed. Because the blood is temporarily removed by the water-vapor bubbles, it is possible to conduct diagnostics or therapy on the intravascular lumen without being affected by the blood. The apparatus according to the present invention includes light irradiating means for diagnostics or therapy in addition to the high-intensity pulsed light irradiating means for producing water-vapor bubbles so that intravascular diagnostics or therapy can be conducted by irradiating light when the blood is temporarily removed. For example, when visible light is used as light for diagnostics or therapy, it is possible to obtain a clear image of the intravascular lumen with an angioscope. Exclusion of the blood is temporary and the blood flows continuously most of time, and therefore the blood flow to peripherals is substantially secured.

When the present specification refers to an angioscope, it also includes a cardioscope and the present invention also includes a cardioscope using a phenomenon that when high-intensity pulsed light of a pulsed laser or the like is irradiated in a blood vessel, the water in the blood absorbs the energy of the high-intensity pulsed light, vaporizes and produces water-vapor bubbles (bubbles induced by high-intensity pulsed light) and the blood in that area is temporarily removed.

Figure 2:
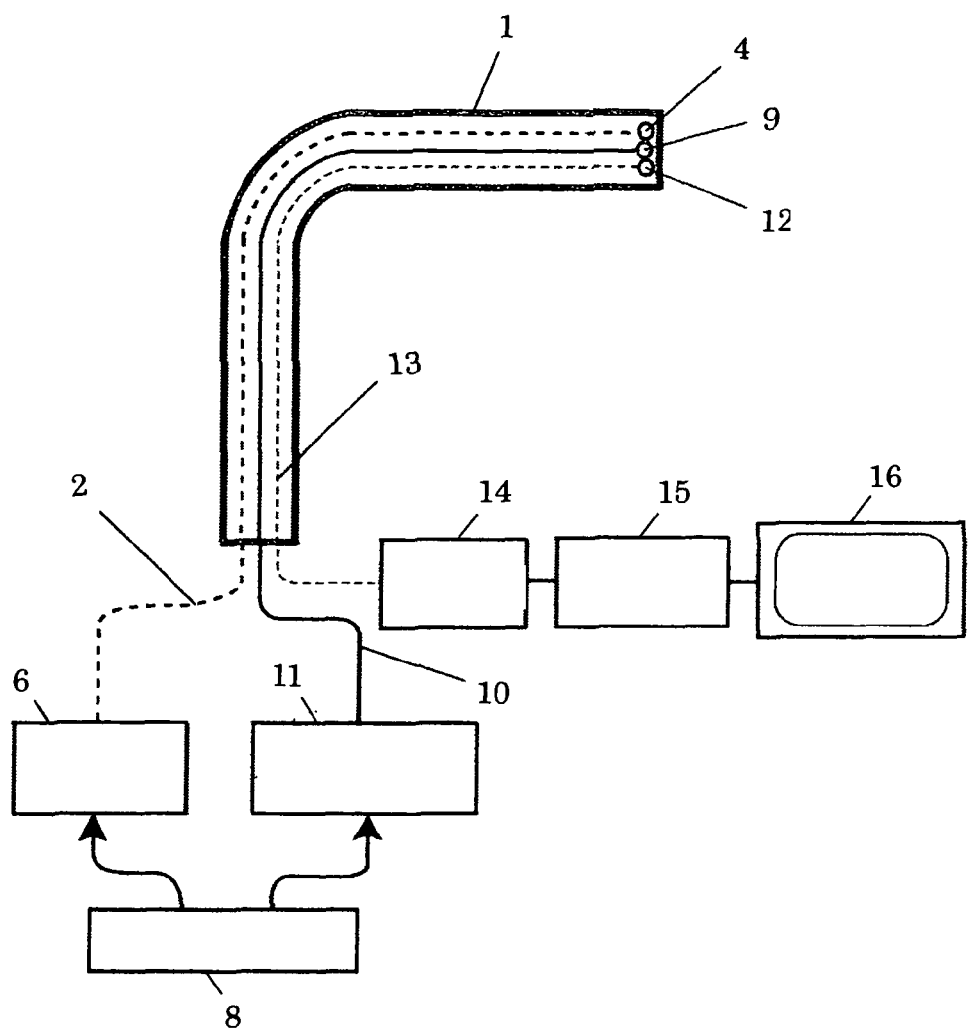
FIG. 2 illustrates an endoscope of the present invention.

FIG. 1 shows a schematic diagram of an intravascular diagnostic or therapeutic apparatus according to the present invention. The intravascular diagnostic or therapeutic apparatus according to the present invention is a catheter-type apparatus including at least a blood vessel catheter 1 (guide catheter), high-intensity pulsed light irradiating means for irradiating high-intensity pulsed light into a blood vessel and light irradiating means for irradiating light for diagnostics or therapy into the blood vessel. The high-intensity pulsed light irradiating means includes high-intensity pulsed light generating means (high-intensity pulsed light source 6), means for transmitting high-intensity pulsed light into the blood vessel and means for irradiating the interior of a blood vessel with high-intensity pulsed light or the like and the part transmitting the high-intensity pulsed light is disposed in the catheter 1 as the high-intensity pulsed light transmitting fiber 2, the means for irradiating the interior of a blood vessel with high-intensity pulsed light is provided at a far end of the light transmitting fiber 2 as a high-intensity pulsed light irradiation section 4. The high-intensity pulsed light irradiation section 4 may be provided with a member for changing an angle of irradiation of pulsed light such as a prism, but no special member is normally required and the far end of the optical fiber can act as the high-intensity pulsed light irradiation section 4. Furthermore, the diagnostic or therapy light irradiating means includes light generating means (light source 7), means for transmitting light into the blood vessel and means for irradiating light into the blood vessel, and the means for transmitting light is provided as the light transmitting fiber 3 for diagnostics or therapy in the catheter and a light irradiation section 5 is provided at the far end thereof as the means for irradiating light into the blood vessel. The light irradiation section 5 may also be provided with a member for diffusing light for diagnostics or therapy, but no special member is normally required and the far end of the optical fiber can act as the light irradiation section 5. Furthermore, there can be a plurality of light irradiating means for diagnostics or therapy, and in this case, they are preferably a plurality of irradiating means for irradiating light of different wavelengths. For example, when it is provided with laser light irradiating means for angioplasty as light irradiating means and visible light irradiating means for looking through the blood vessel, it is possible to observe therapeutic effects of an intravascular lumen through irradiation of visible light, which has been cured through laser light irradiation. FIG. 2 shows a schematic diagram of an angioscope which is an example of the intravascular diagnostic or therapeutic apparatus of the present invention. The angioscope of the present invention is a catheter-type apparatus including at least an angioscopic catheter 1 (guide catheter), high-intensity pulsed light irradiating means for irradiating high-intensity pulsed light into a blood vessel, illumination light irradiating means for pulsed-illuminating the interior of the blood vessel to enable optical observation and image-pickup means for taking images of an intravascular lumen illuminated with the illumination light. The high-intensity pulsed light irradiating means is as described above. Furthermore, the illumination light irradiating means includes illumination light generating means (pulse illumination light source 11), means for transmitting illumination light into the blood vessel and means for irradiating illumination light into the blood vessel, and the means for transmitting illumination light is provided as a lightguide 10 including a light transmitting fiber in the catheter and an illumination section 9 is provided at a far end thereof as means for irradiating illumination light into the blood vessel. The illumination section 9 may also be provided with a member or the like for diffusing illumination light but no special member is normally required and the far end of the optical fiber can act as the illumination section 9. The image-pickup means includes means for receiving an image of the intravascular lumen, means for transmitting the image of the intravascular lumen, means for converting the image to an electric signal (image processing means), means for monitoring the image or the like and further includes lenses or the like for forming the intravascular lumen image and optically enlarging the image. The means for transmitting the image of the intravascular lumen is provided as an image guide 13 including the light transmitting fiber in the catheter, an observation section 12 as means for receiving the image of the intravascular lumen is provided at a far end of the image guide 13 and lenses are provided at the observation section 12 as required. The means for converting the image to an electric signal includes an image pickup device 14 and an image processing section 15 and the means for monitoring the image includes a monitor 16 or video or the like.

Furthermore, the intravascular diagnostic or therapeutic apparatus of the present invention may also include a liquid feeding system for injecting saline or the like into a blood vessel. The liquid feeding system sends a small amount of saline or the like and replaces local blood irradiated with high-intensity pulsed light by the saline or the like.

Furthermore, the intravascular diagnostic or therapeutic apparatus of the present invention may also be an apparatus capable of moving the end of the catheter 1 using a wire or torque tube, that is, an apparatus having irradiation field operability. When the diagnostic or therapeutic apparatus of the present invention is an angioscope, it is called an "endoscope having field of view operability" or "field of view adjustable endoscope."

Figure 3:
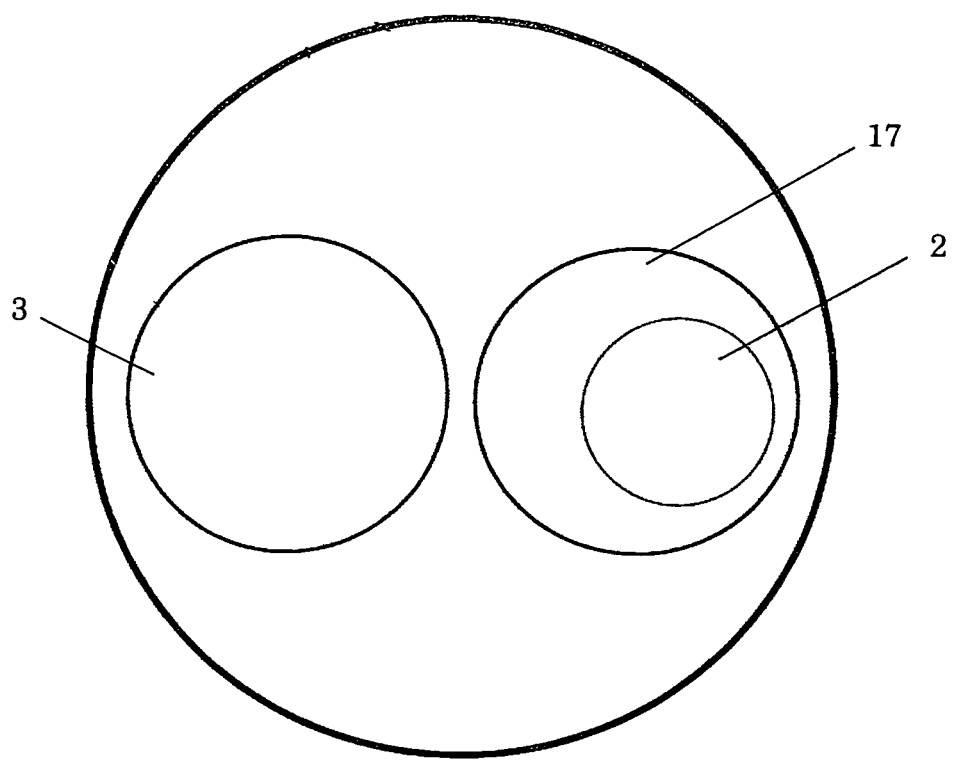
FIG. 3 illustrates a cross section of a catheter part of the intravascular diagnostic or therapeutic apparatus according to the present invention.
Figure 4:
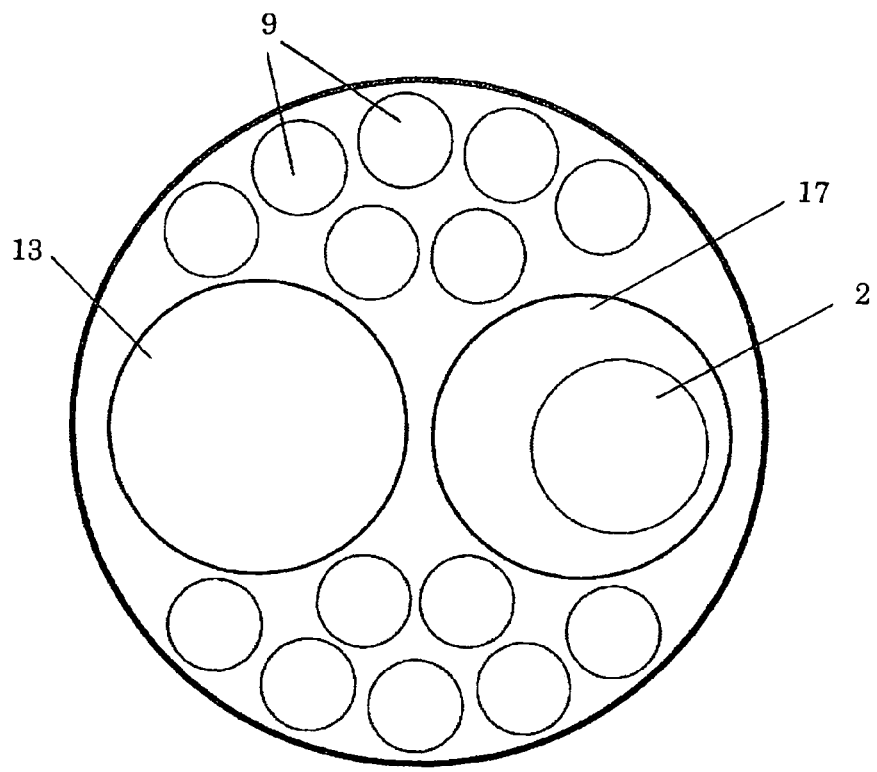
FIG. 4 illustrates a cross section of a catheter part of the endoscope according to the present invention.

The blood vessel catheter 1 is a cylinder for inserting part of the diagnostic or therapeutic apparatus of the present invention into a blood vessel and is used as a guide when moving part of the diagnostic or therapeutic apparatus to a desired region. A common catheter can be used for the catheter 1, the diameter or the like is not limited and can be designed according to the thickness of the blood vessel to be observed as appropriate. The catheter 1 is constructed of a high-intensity pulsed light transmitting fiber 2, light transmitting fiber 3 for diagnostics or therapy, lightguide 10 and further the image guide 13 when the apparatus of the present invention is an angioscope, and these fiber and guide are incorporated in the catheter 1. The respective guides are constructed of a transmission optical fiber or the like. The way the fiber and guide are combined is not limited. For example, these fiber and guide may be incorporated in the catheter 1 at random or a plurality of lumens may be provided in the catheter 1 and the respective guides may be incorporated therein. Or there may be a plurality of light transmitting fibers 3 for diagnostics or therapy or lightguides 10, high-intensity pulsed light transmitting fibers 2 and image guides 13 and it is particularly preferable that there be a plurality of light transmitting fibers 3 for diagnostics or therapy or lightguides 10 to irradiate light of different wavelengths as described above. Furthermore, when the apparatus of the present invention is an angioscope, the presence of a plurality of lightguides allows pulsed illumination over a wide range of the interior of a blood vessel. The plurality of lightguides 10 are preferably distributed in the catheter 1. Furthermore, there may also be a plurality of high-intensity pulsed light transmitting fibers 2, and in this case, by simultaneously irradiating high-intensity pulsed light of a low degree of intensity that does not adversely affect the blood vessel wall or the like, it is possible to generate water-vapor bubbles large enough to observe the intravascular lumen without damaging the blood vessel wall. Even when a plurality of high-intensity pulsed light transmitting fibers 2 are included, it is possible to provide the fibers in a distributed manner. FIG. 3 illustrates a sectional view of the intravascular diagnostic or therapeutic apparatus of the present invention. Furthermore, FIG. 4 shows a sectional view of an angioscope, which is an example of the diagnostic or therapeutic apparatus of the present invention. FIG. 4 illustrates an endoscope including the image guide 13, laser transmission fiber 2 disposed in a liquid feeding lumen 17 and a plurality of lightguides 10, but this is only an example and the arrangement of each fiber and guide is not limited to that shown in FIGS. 3 and 4.

Examples of the high-intensity pulsed light include pulsed light generated by a laser and optical parametric oscillator (OPO).

For the laser generating means, a common laser generator can be used and any type of laser can be used if it has at least a wavelength band with a water absorbing coefficient of 10 to 1000 $cm^{-1}$ or preferably 10 to 100 $cm^{-1}$ and it is possible to use a solid laser or XeCl excimer laser using rare-earth ions or the like. Furthermore, the oscillating wavelength of the laser may be 0.3 to 3 µm, preferably 1.5 to 3 µm, more preferably 1.5 to 2.5 µm or most preferably a wavelength close to a water absorbing wavelength (1.9 µm). A laser is represented by ions of an element that generates laser and the type of a base material that retains the ions and examples of such elements include Ho (holmium), Tm (thulium), Er (erbium), Nd (neodymium) which belong to rare earths and among them, Ho and Tm are preferable. Examples of the base material include YAG, YLF, YSGG, YVO or the like. For example, Ho:YAG laser, Tm:YAG laser, Ho:YLF laser, Tm:YLF laser, Ho:YSGG laser, Tm:YSGG laser, Ho:YVO laser, Tm:YVO laser and XeCl excimer laser (oscillating wavelength 308 nm) or the like can be used. Among them, Ho:YAG laser (oscillating wavelength 2.1 µm), Tm:YAG laser (oscillating wavelength 2.01 µm) having a laser oscillating wavelength approximate to the water absorbing wavelength (1.9 µm) or the like are preferable. Furthermore, Ho:YAG laser having a relatively small absorbing coefficient with respect to tissue of a living body, large optical penetration depth and generating large water-vapor bubbles is preferable.

Examples of the laser generator include LASER 1-2-3 SCHWARTZ (manufactured by ELECTRO-OPTICS).

The optical parametric oscillator (OPO) should be able to change the wavelength of pulsed light continuously and pulsed light having a wavelength band with a water absorbing coefficient of 10 to 1000 $cm^{-1}$ can be selected. For example, a wavelength of approximately 0.3 to 3 µm, preferably 1.5 to 3 µm, more preferably 1.5 to 2.5 µm, or most preferably the water absorbing wavelength (1.9 µm) may be selected.

The relative position of the far end of the high-intensity pulsed light transmitting fiber 2 from which high-intensity pulsed light is irradiated (high-intensity pulsed light irradiation section 4) with respect to the far end of the catheter 1 is not limited, either and the far end of the high-intensity pulsed light transmitting fiber 2 (high-intensity pulsed light irradiation section 4) may protrude from the far end of the catheter 1 or the far end of the high-intensity pulsed light transmitting fiber 2 (high-intensity pulsed light irradiation section 4) may be withdrawn within the range of the catheter 1 or the far end of the high-intensity pulsed light transmitting fiber 2 (high-intensity pulsed light irradiation section 4) may be located at the same position as the far end with respect to the horizontal direction of the catheter 1. For example, when the far end of the high-intensity pulsed light transmitting fiber 2 (high-intensity pulsed light irradiation section 4) is withdrawn within the catheter 1 and prevented from protruding outward, generation of water-vapor bubbles starts within the catheter 1, and therefore there is an advantage that water-vapor bubbles do not extend sideward and do not produce a strong physical pressure to the intravascular lumen. Thus, by adjusting the relative position of the far end of the high-intensity pulsed light transmitting fiber 2 (high-intensity pulsed light irradiation section 4) with respect to the far end of the catheter 1, it is possible to control the sideward extension of water-vapor bubbles.

Blood absorbs a large amount of high-intensity pulsed light and sizes of water-vapor bubbles generated in blood are smaller than those in water. Therefore, when local blood into which high-intensity pulsed light is irradiated to generate water-vapor bubbles is irradiated with high-intensity pulsed light, it is desirable to replace the blood with a liquid such as saline or the like whose osmotic pressure is approximate to that of a body fluid having small absorption of high-intensity pulsed light. As such a liquid, infusion such as dialysate is used in addition to saline. By replacing the blood with such a liquid, the energy of the high-intensity pulsed light is absorbed by the liquid sufficiently, easily producing water-vapor bubbles in sufficient sizes for observation of the intravascular lumen. In this case, it is possible to incorporate solution feeding means in the catheter of the angioscope of the present invention and inject saline or the like into the part in the blood vessel into which high-intensity pulsed light is irradiated, that is, the neighborhood of the part irradiated with high-intensity pulsed light using the solution feeding means. The solution feeding means is constructed of a liquid feeding channel provided in the catheter, an injection port provided at a far end of the liquid feeding channel, a liquid reservoir connected to the channel and a liquid feeding pump or the like. As the liquid feeding channel, it is also possible to provide a lumen 17 in the catheter and use the lumen 17 as the liquid feeding channel or provide a separate channel tube in the catheter 1. In this case, high-intensity pulsed light is irradiated into the blood vessel and the local blood portion in the blood vessel in which high-intensity pulsed light is irradiated and water-vapor bubbles start to generate is replaced by saline or the like, and therefore the part in the blood vessel into which high-intensity pulsed light of the high-intensity pulsed light irradiating means is irradiated and the injection port of the solution feeding means need to be located close to each other. For example, it is possible to provide the lumen 17 in the catheter 1, pass the high-intensity pulsed light transmitting fiber 2 therethrough and allow saline or the like to be sent through the lumen 17. The amount of saline to be sent is not limited, but an amount of approximately 1/10 to 1/1000 of the amount of liquid to be sent observed by the endoscope with a conventional fluid injected is sufficient. For example, the conventional method of injecting a fluid requires the fluid of 1 to 2 mL/sec to be injected, but the amount of injection according to the present invention required is no more than approximately 1 mL/min. Liquid feeding to this extent never interferes with the blood flow and can secure the supply of oxygen to peripherals.

The means for transmitting high-intensity pulsed light into the blood vessel includes means for irradiating high-intensity pulsed light (high-intensity pulsed light irradiation section 4) located near the far end of the catheter 1 and a quartz fiber (optical fiber) (high-intensity pulsed light transmitting fiber 2) which transmits high-intensity pulsed light from a high-intensity pulsed light generator to the high-intensity pulsed light irradiating means. The term "near the far end" in the present specification means a part near an end opposite to the end (near-end part) connected to the high-intensity pulsed light generator and refers to the far end part and a part approximately several tens of cm from the far end part.

The quartz fiber is included in the catheter 1 and connected to the high-intensity pulsed light generator at one end and connected to the high-intensity pulsed light irradiating means (high-intensity pulsed light irradiation section 4) at the other end. The quartz fiber used in the present invention ranges from an extremely thin one having a diameter 0.05 to 0.3 mm to one having a visible thickness and quartz fibers of a wide variety of diameters can be used if they can be at least accommodated in the catheter 1 and can transmit high-intensity pulsed light energy.

The high-intensity pulsed light irradiating means is the means for irradiating the interior of a blood vessel with high-intensity pulsed light and irradiating high-intensity pulsed light generated by the high-intensity pulsed light generator (high-intensity pulsed light source 6) outside the body and transmitted through the quartz fiber (high-intensity pulsed light transmitting fiber 2) along the blood vessel into the blood vessel so as to form water-vapor bubbles. In this case, the direction of irradiation of high-intensity pulsed light is not limited. Furthermore, a plurality of high-intensity pulsed light transmitting fibers 2 can be provided in a distributed manner as described above.

The maximum size of water-vapor bubbles generated through irradiation of high-intensity pulsed light is approximately 4 mm in diameter in horizontal direction, approximately 5 mm in length in longitudinal direction and their presence time is approximately 100 is to 300 µs. The size of water-vapor bubbles generated can be controlled by changing the intensity of high-intensity pulsed light and diameter of the fiber for irradiating high-intensity pulsed light, and when there are a plurality of high-intensity pulsed light transmitting fibers, the size of water-vapor bubbles generated can also be controlled by adjusting their arrangement. The intensity of high-intensity pulsed light, diameter of the fiber and arrangement of the plurality of fibers can be set as appropriate according to the thickness of the blood vessel to be observed. The diameter of the fiber is preferably 100 µm to 1000 µm.

The intensity (pulse energy) of high-intensity pulsed light is not limited, but can be set as appropriate.

The pulse width of high-intensity pulsed light is not limited, either, but this may be 10 ns to 10 ms, preferably 100 µs to 1 ms or more preferably 150 µs to 250 µs. Note that the pulse width is expressed with full width at half maximum.

Irradiation of high-intensity pulsed light is preferably synchronized to delay from pulsating of blood flow, that is, a pulsating blood flow. A blood flow is a pulsating flow and when blood is flowing, that is, when kinetic energy (dynamic pressure) of blood is large, exclusion of blood due to bubbles affects not only blood pressure (static pressure) but also dynamic pressure and it is difficult to remove a large volume of blood. On the contrary, when blood stops completely, since blood is a non-Newtonian fluid, viscosity thereof increases, which also makes it difficult to remove blood due to bubbles. Therefore, when the pulsating blood flow starts to decrease (before the blood flow stops), there is a most suitable timing for exclusion of blood. This timing can be detected by setting a delay time specific to the blood vessel observed in heart beat information from an electrocardiogram. In this case, it is possible to electronically connect the electrocardiograph and laser generator and transmit an electrocardiogram signal to the high-intensity pulsed light generator through a delay generator so that high-intensity pulsed light is irradiated when the pulsating blood flow decreases. It is possible to determine the delay time to be applied through a combination of the electrocardiograph, delay generator and high-intensity pulsed light generator as appropriate. The timing for transmitting a signal in such a way that high-intensity pulsed light is irradiated at a time at which the pulsating blood flow in the electrocardiograph decreases can also be easily determined by those skilled in the art from a publicly known relationship between a cardiac cycle, aorta blood flow and electrocardiogram. For example, in the case of a coronary artery, substantially no blood flows at a contraction phase in which the aorta blood flow is large and blood flows at diastole in which the coronary artery blood flow is small. Therefore, the timing at which the coronary artery blood flow becomes a maximum is preferably after emergence of a T wave before emergence of a P wave in the electrocardiogram and the irradiation timing of high-intensity pulsed light is preferably after the emergence of the P wave until disappearance of a QRS wave. Furthermore, it is also possible to provide a pressure sensor or the like in the catheter of the endoscope of the present invention and monitor the pulsating blood flow through the sensor so that high-intensity pulsed light is irradiated when the pulsating blood flow decreases. In this case, the pressure sensor and high-intensity pulsed light generator are also electronically connected together and the signal from the pressure sensor is transmitted to the high-intensity pulsed light generator with a delay. Light for diagnostics or therapy such as pulse illumination light may also be adapted so as to transmit a signal from the high-intensity pulsed light generator and be irradiated with a delay or transmit a signal from the electrocardiograph or pressure sensor and be irradiated from the high-intensity pulsed light generator with a further delay. The delay time in this case can also be set as appropriate. A preferable delay time varies depending on laser irradiation conditions or the like, but it is, for example, several tens of us to several hundreds of μs and it is possible to actually use the apparatus of the present invention, change the delay time in the blood vessel to be observed, carry out irradiation of laser and irradiation of illumination light and select a time at which the most appropriate image can be obtained.

Figure 6:
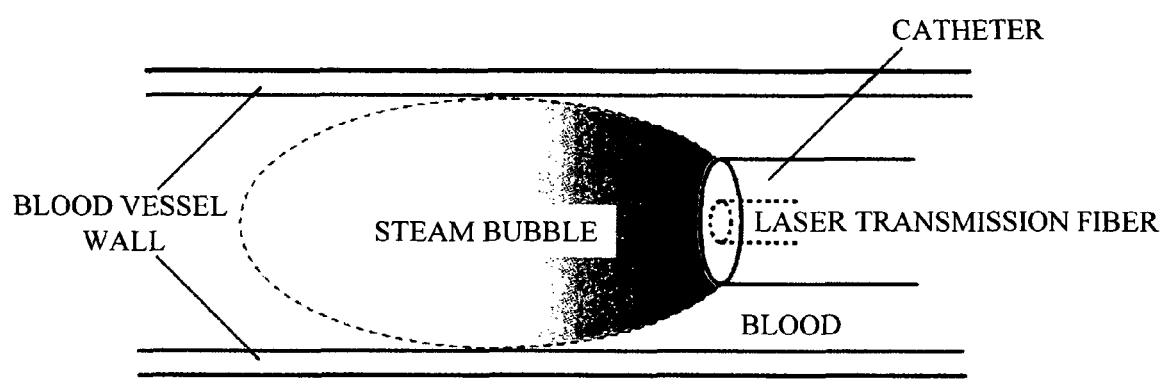
FIG. 6 illustrates water-vapor bubbles induced by a laser.

FIG. 6 shows a schematic view of water-vapor bubbles generated by the endoscope of the present invention. As shown in the figure, laser is irradiated from the laser transmission fiber 2 in the catheter 1 and water-vapor bubbles are generated in an area in front of the catheter 1.

As described above, the water-vapor bubble generation time is as short as approximately 200 μs to 300 μs and water-vapor bubbles cannot be spotted by the naked eye. Therefore, in order to irradiate light for diagnostics or therapy into the intravascular lumen in an extremely short time during which bubbles are produced and blood is removed and produce the effect, for example, in order to irradiate visible light and observe the intravascular lumen, the interior of the blood vessel is pulse-illuminated with an irradiation flash lamp simultaneously with the generation of water-vapor bubbles. For example, in the case of the endoscope which irradiates visible light, the interior of the blood vessel is pulse-illuminated and images are taken with time-resolved photography. For this purpose, a delay can be provided between irradiation of high-intensity pulsed light and irradiation of pulsed irradiation light for diagnostics or therapy. In order to provide a delay, for example, a delay pulse generator 8 can be used. The delay time can be set as appropriate according to the combination of the high-intensity pulsed light generator used and diagnostic or therapeutic light irradiation apparatus and according to the pulse width or the like of high-intensity pulsed light in such a way that pulse irradiation is performed when the size of water-vapor bubbles is close to a maximum level.

The light used as light for diagnostics or therapy by the intravascular diagnostic or therapeutic apparatus of the present invention is not limited and various kinds of light can be used according to the purpose. Various types of diagnostics and therapy are available according to the wavelength of light and type of the light source. Conventionally, various types of therapy are conducted using a balloon catheter with light irradiating means, stopping a blood flow by expanding the balloon and irradiating light. Furthermore, various types of therapy are conducted by irradiating light through a light irradiation section of light irradiating means which is in contact with an intravascular lumen wall. Use of the apparatus of the present invention makes it possible to irradiate light and conduct various types of therapy without stopping the blood flow or without causing the light irradiation section to contact the intravascular lumen wall. Therefore, all publicly known diagnostics or therapy of an intravascular lumen through irradiation of light can be conducted using the apparatus of the present invention.

As the light for diagnostics or therapy, it is possible to use any one of ultraviolet light, visible light, near-infrared light and infrared light. Furthermore, it is also possible to use light generated by a solid laser, semiconductor laser, dye laser, variable wavelength near-infrared laser, optical parametric oscillator (OPO) or Raman laser, light generated by coupling a non-linear optical converter with these lasers and a flash lamp. Here, the light that can be generated by coupling the non-linear optical converter refers to light obtained by passing light generated from a light source through the non-linear optical converter. Furthermore, the light for diagnostics or therapy may also be high-intensity light.

Diagnostics and therapy of an intravascular lumen which can be conducted using the apparatus of the present invention are not limited, but the following diagnostics, therapy can be included, for example.

By irradiating visible light, it is possible to obtain an image of an intravascular lumen and conduct various types of diagnostics. In this case, the apparatus of the present invention can be used as an angioscope. As the visible light in this case, a flash lamp can be used. The angioscope will be described later.

Ultraviolet light having a wavelength of 400 nm or less can be used for relaxation of blood vessels. When hemorrhage occurs in tissue due to a subarachnoid hemorrhage or the like, surroundings of the blood vessel of the tissue are covered with blood, which causes the blood vessel to contract, producing a blood vessel contraction. In this case, by irradiating weak ultraviolet light, it is possible to relax the blood vessel and inhibit the contraction. For relaxation of the blood vessel, 325 nm ultraviolet light is irradiated using, for example, a continuous ultraviolet He—Cd laser. The average optical energy irradiated onto the blood vessel wall in this case is preferably 10 mJ/mm$^2$ (Kanji Nakai et al., Cerebral Blood Vessel Contraction, VOL. 14, 46 Blood Vessel Contraction Inhibition Effect by Low-Output Ultraviolet Preventive Irradiation, Chugai Igakusha Co., Ltd., published Jun. 10, 1999). Furthermore, KrF (krypton-fluoride) excimer laser (wavelength 248 nm) may also be irradiated. Irradiation can be conducted at a rate of 0.1 to 10 mJ/pulse/mm$^2$ with an iterative number of 1 to several hundreds Hz (Yuji Morimoto et al., Photochemistry and photobiology, 1998, 68(3): 388-393). Moreover, it is also possible to irradiate 351 nm ultraviolet light using an argon ion laser (H. Matsuo et al., Lasers Med Sci 2000, 15: 181-187). The light irradiation condition for relaxing the blood vessel can also be determined with reference to Yuji Morimoto et al., Proceedings of Laser-Tissue Interaction VII, 126/SPIE, Vol. 2681; Yuji Morimoto et al., Proceedings of Laser-Tissue Interaction VIII, SPIE Vol. 2975; Kanji Nakai et al., Proceedings of Laser-Tissue Interaction IX, SPIE, Vol. 3254; Yuji Morimoto et al., Proceedings of Laser-Tissue Interaction X: Photochemical, Photothermal, and Photomechanical, SPIE Vol. 3601 or the like.

On the other hand, in contrast to ultraviolet light, when infrared light is irradiated from a near-infrared region having a wavelength 800 nm or above, heat is produced in the irradiated part and it is possible to contract the blood vessel. For example, it is possible to stop a blood flow due to a blood vessel contraction by irradiating infrared light from the near-infrared region in the blood vessel in the tissue affected by a cancer and thereby stop a nutrient supply to the cancer cell and kill the cancer cell. For example, 800 nm light can be irradiated using a titanium sapphire laser.

Furthermore, it is also possible to relax or contract the blood vessel through irradiation of visible light. For example, a laser light having a wavelength 458 nm or 514.5 nm can be irradiated using an argon ion laser (H. Matsuo et al., Lasers Med Sci 2000, 15: 181-187). Furthermore, it is also possible to contract the blood vessel through irradiation of weak ultraviolet light.

Irradiating ultraviolet light, visible light, near-infrared light or infrared light by changing the intensity as appropriate makes it possible to control the relaxation and contraction of the blood vessel.

Furthermore, it is possible to irradiate laser light using the intravascular diagnostic or therapeutic light irradiating means of the present invention, destroy atheroma of arterial sclerosis or thrombus in the blood vessel and conduct angioplasty. The angioplasty refers to a therapy from the interior of the blood vessel by destroying atheroma for the narrowed blood vessel whose blood vessel lumen is narrowed (constriction) due to arterial sclerosis or destroying thrombus formed in the blood vessel. The angioplasty using a laser is a method for curing constriction or obstruction by inserting a laser catheter into the constricted (narrowed) or obstructed (blocked) artery and transpiring or burning the lesioned part using the energy of laser light. When angioplasty is conducted using the apparatus of the present invention, Ho:YAG laser (wavelength 2.08 µm), xenon chloride excimer laser (wavelength 0.308 µm), $CO_2$ laser (wavelength 10.6 µm), Nd:YAG laser (wavelength 1.06 µm) can be irradiated to the lesioned part as light for diagnostics or therapy (G. J. Gillen et al., Journal of Medical Engineering & Technology, Volume 8, Number 5 (September/October 1984), pages 215-217; MICHAEL ELDAR et al., JACC Vol. 3, No. 1 Jan. 1984: 135-7; Karl K. Haase et al., Lasers in Surgery and Medicine 11:232-237 (1991)).

Furthermore, it is also possible to alleviate atheroma and cure arterial sclerosis by cutting ester bond of cholesterol accumulated in the atheroma of arterial sclerosis. In this case, free electron laser (wavelength 5.75 µm) can be irradiated.

With regard to the wavelength of specific light to be irradiated, light from a flash lamp may be passed through a filter having a specific wavelength and only the light having the desired wavelength may be transmitted through an optical fiber. Furthermore, it is also possible to irradiate light having a specific wavelength using pulsed light generated by an optical parametric oscillator (OPO), which is high-intensity pulsed light also used to generate water-vapor bubbles.

Furthermore, the apparatus of the present invention can also be used for photochemical therapy (PDT, also referred to as "photodynamic therapy"). Here, the PDT (photochemical therapy) refers to a therapy whereby a photosensitizer (PDT agent) having affinity with a specific lesioned part is specifically accumulated in the lesioned part and irradiated with light having a specific wavelength to thereby selectively damage and annihilate tissue of the lesioned part. There is a proposal on a mechanism whereby a photosensitizer trapped in a lesioned part is excited through irradiation with light, the energy of the photosensitizer is transferred to oxygen in the lesioned part, active singlet oxygen is generated and the active oxygen necroses the cell of the lesioned part. The PDT can damage and annihilate atheroma in arterial sclerosis and thereby cure the arterial sclerosis.

The PDT requires the photosensitizer (PDT agent) which can be accumulated in the lesioned part to be administered, but the PDT agent combined with the apparatus of the present invention is not limited and a publicly known PDT agent can be used in combination with light having an absorption wavelength thereof. As such a PDT agent, various types of porphyrin derivative are reported (JP Patent Publication (Kokai) No. 9-124652 A, WO98/14453, JP Patent Publication (Kokai) No. 4-330013 A, JP Patent No. 2961074). Furthermore, ATX-S10 (670 nm) (Iminochlorin aspartic acid derivative which is a chlorin-based agent (TOYO HAKKA KOGYO CO., LTD., rights transferred to PHOTOCHEMICAL COMPANY in 2000, JP Patent Publication (Kokai) No. 6-80671), NPe6 (664 nm) (mono-L-aspartyl chlorin e6, JP Patent No. 2961074), mTHPC (652 nm), SnET2 (660 nm) (tin etiopurpurin, Miravant Medical Technologies), AlPcS (675 nm) (chloro aluminum sulphonated phthalocyanine), BPD-MA (690 nm) (benzoporphyrin derivative monoacid ring A, QLT Inc.), Lu-tex (732 nm) (Lutetium Texaphyrin) or the like can also be preferably used (common name, absorption wavelength are shown and also general name, place to obtain, documents are shown).

When these agents are administered, the agents are dissolved into an appropriate buffer solution such as a phosphate buffer salt solution and a pharmaceutically allowed additive is added as required. Examples of such an additive include solubilizer such as organic solvent, pH adjustor such as acid and base, stabilizer such as ascorbic acid, diluting agent such as glucose, tonicity adjusting agent such as sodium chloride or the like. The method of administration is not limited and the additive can be administered through intravenous injection, intramuscular injection, hypodermic injection, oral administration or the like. Furthermore, to reduce sunburn after the administration, the additive can also be administered directly to the lesioned part. For example, when the disease to be cured is arterial sclerosis or prostatic hypertrophy, agent administration means such as a needle and agent injection part are disposed in a blood vessel catheter or urethral catheter and the agent may be administered locally as a drug delivery catheter. The dosage of the PDT agent is not limited and when systemic administration is applied through intravenous injection or the like, the dosage is preferably 0.01 to 100 mg/kg body weight, preferably 1 to 5 mg/kg body weight. In the case of local administration, an agent prepared, for example, to several μg/ml to several mg/ml can be administered directly to the lesioned part through injection or the like.

When a PDT is conducted using the apparatus of the present invention, it is possible to leave a PDT agent accumulated in a lesioned part such as atheroma of arterial sclerosis of the blood vessel wall beforehand as described above, then irradiate high-intensity pulsed light using the apparatus of the present invention, generate water-vapor bubbles in the blood vessel, temporarily remove blood and irradiate light that can be absorbed by the PDT agent as light for diagnostics or therapy. In the apparatus of the present invention, the type of light to be irradiated for the therapy is not limited, but continuous or pulsed laser light or variable wavelength light generated by an optical parametric oscillator (OPO) is preferable. The wavelength for irradiation ranges from 600 nm to 800 nm and light having a wavelength close to the absorption wavelength of the PDT agent used can be used. The wavelength of light generated by the OPO in particular can be changed and is adaptable to various types of PDT agents. As the laser, a semiconductor laser, dye laser, double-frequency wave of a variable wavelength near-infrared laser or the like can be used preferably. The apparatus of the present invention irradiates light for diagnostics or therapy when water-vapor bubbles are generated, and therefore irradiation light is also adapted to the generation of water-vapor bubbles and converted to pulsed light. Here, pulsed light refers to light whose pulse width is 1 ms or less. Furthermore, continuous light is interrupted using a light chopper and can also be irradiated as pulsed light.

Hereinafter, an angioscope using visible light, which is an example of the intravascular diagnostic or therapeutic apparatus according to the present invention will be explained in detail based on FIG. 2. Though other blood vessel diagnostic or therapeutic apparatuses of the present invention differ in that the type of light to be irradiated for diagnostics or therapy is different and no image-pickup means is required, they can be designed/assembled in the same way as for an angioscope and can be used by similar methods.

The pulsed illumination means includes an illumination light generator having a flash xenon chloride lamp, flash halogen lamp or the like as the pulse illumination light source 11, infrared cut filter, light control shutter, condenser lens and optical fiber or the like which transmits illumination light from a light source to the part from which illumination light is irradiated into the blood vessel. The illumination light generator and the optical fiber are connected together, illumination light generated by the illumination light generator and condensed by the condenser lens is introduced into the optical fiber, passed through the lightguide 10, transmitted to the interior of the blood vessel to be observed and the interior of the blood vessel is illuminated from the far end of the optical fiber. As the optical fiber, one made of quartz glass can be used as in the case of the high-intensity pulsed light irradiating means. Moreover, instead of the illumination light generator, an LED (Light Emitting Diode) can also be provided at the far end of the catheter and a delay can be provided between light emission of the LED and irradiation of high-intensity pulsed light for control in this case, too.

The pulse width of the pulse illumination light is set to be smaller than the pulse width of the high-intensity pulsed light. Such a setting allows pulsed illumination to be performed while water-vapor bubbles exist and allows reliable image pickup.

The position of the far end (illumination section 9) of the lightguide 10 with respect to the far end of the catheter 1 is not limited, the far end (illumination section 9) of the lightguide 10 can protrude from the far end of the catheter 1 or the far end (illumination section 9) of the lightguide 10 can withdraw within the catheter 1 or the far end (illumination section 9) of the lightguide 10 can be located at the same position as the far end with respect to the horizontal direction of the catheter 1. For example, when the far end (illumination section 9) of the lightguide 10 protrudes from the far end of the catheter 1, the interior of the blood vessel can be illuminated without any shadow being produced in the catheter 1, which is advantageous.

It is possible to obtain an image of an intravascular lumen as a still image through pulsed illumination when high-intensity pulsed light is irradiated, water-vapor bubbles are generated until the water-vapor bubbles disappear or more preferably when the size of water-vapor bubbles is close to a maximum. Furthermore, high-intensity pulsed light is irradiated at a certain pulse rate, water-vapor bubbles are generated continuously, water-vapor bubbles are generated continuously and pulse-illuminated simultaneously with the generation of water-vapor bubbles, and it is thereby possible to obtain images of the intravascular lumen as moving images. The pulse rate at this time is, for example, approximately 20 Hz.

Images of the intravascular lumen can be obtained by the image-pickup means. In the image-pickup means, the optical fiber, image pickup device 14, image processing section 15, monitor 16 or the like are connected and an objective lens such as Celfoc lens is provided at the far end of the optical fiber, constituting an observation section 12. The image of the intravascular lumen is entered into the lens set at the far end of the image guide 13 of the catheter 1 as reflected light, transmitted through the optical fiber and visualized as the image of the intravascular lumen.

In this case, the image light of the intravascular lumen is condensed by the objective lens in the observation section 12 at the far end of the image guide 13, passed through the optical fiber and an image is formed on the image pickup device 14 of a TV camera. In this case, an eyepiece may be provided between the lens and TV camera. The eyepiece is an apparatus which forms the image passed through the image guide 13 on the image pickup device 14 of the TV camera and is provided with a magnifier, focusing function, magnification adjusting function, image rotation function, optical axis adjusting function or the like as required. Any TV camera can be used if it at least includes the image pickup device 14 such as a CCD. In this case, by synchronizing the gate of the CCD with the generation of water-vapor bubbles through a pulse generator, it is possible to obtain an image of the intravascular lumen. When an image is taken, it is possible to observe the intravascular lumen wall of the part where blood is removed by water-vapor bubbles generated.

In this case, the position of the intravascular lumen for image pickup can be the same as the direct sight direction for a normal blood vessel, but when the angioscope is a cardioscope targeted for the heart or targeted for a thick blood vessel, it is possible to set the position freely by changing the orientation or the like of the lens. A change of the orientation of the lens or focusing of the lens can be performed using a motor or the like. Furthermore, it is also possible to change the observation direction of the intravascular lumen using a prism or the like. The image formed on the image pickup device 14 is displayed on the monitor 16 and the image is recorded or saved in a video as required.

Figure 7:
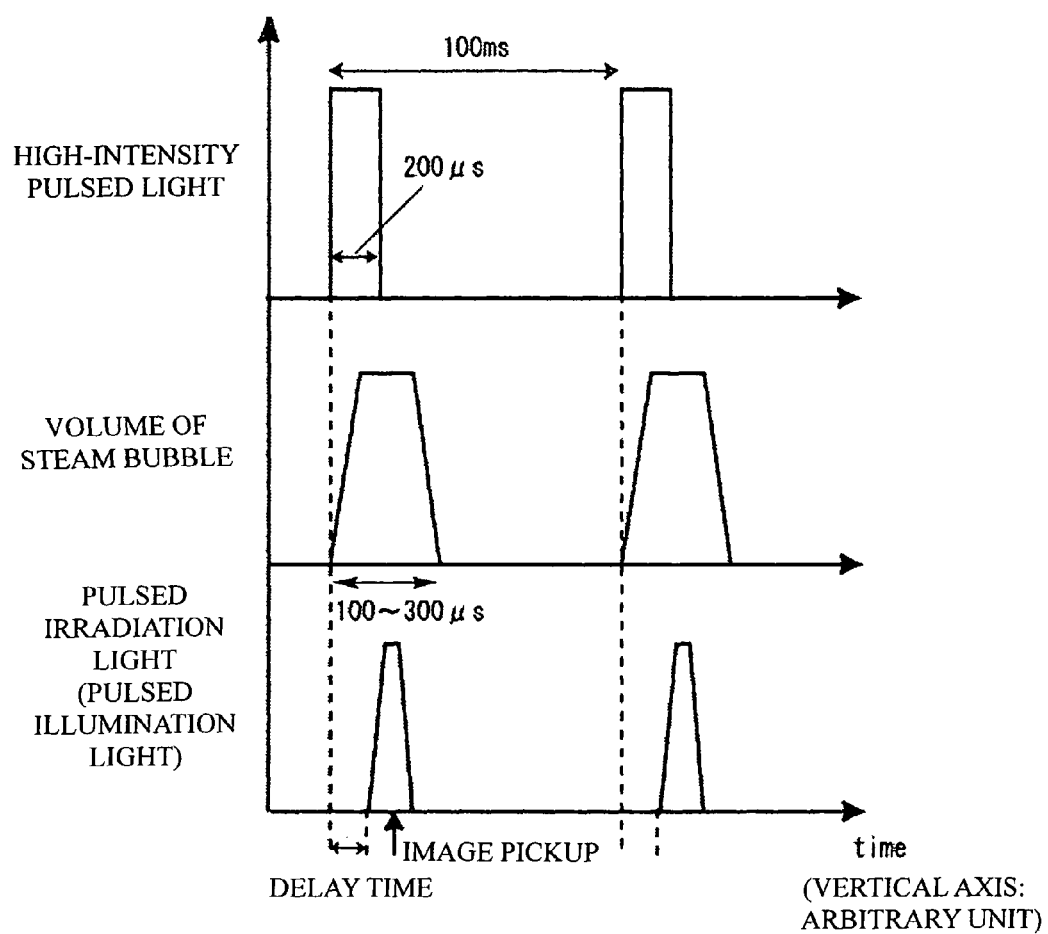
FIG. 7 illustrates a temporal relationship between irradiation of high-intensity pulsed light, generation of water-vapor bubbles and illumination light flashing.

FIG. 7 shows an example of a temporal relationship between irradiation of high-intensity pulsed light, generation of water-vapor bubbles and irradiation of pulsed light for diagnostics or therapy (pulsed illumination for illumination in the case of an angioscope). As shown in the figure, high-intensity pulsed light is irradiated with a pulse width of 200 µs, water-vapor bubbles are generated simultaneously with irradiation of pulsed light and its volume decreases after the volume increases up to a maximum and water-vapor bubbles disappear in 100 to 300 µs after the generation. Pulsed irradiation light for diagnostics or therapy is emitted with a certain delay with respect to the irradiation of high-intensity pulsed light so that it is irradiated when the volume of water-vapor bubbles approximates to a maximum. The pulse width of the pulsed irradiation light is smaller than the pulse width of the high-intensity pulsed light so that the pulsed irradiation light can act (image pickup in the case of the angioscope) when the volume of water-vapor bubbles approximates to a maximum. By repeating the irradiation of the high-intensity pulsed light, generation of water-vapor bubbles and pulse irradiation for diagnostics or therapy at short intervals, it is possible to effectively conduct diagnostics or therapy of the intravascular lumen and obtain images as moving images in the case of the angioscope in particular.

The position of the far end (observation section 12) of the image guide 13 with respect to the far end of the catheter 1 is not limited and the far end (observation section 12) of the image guide 13 may protrude from the far end of the catheter 1 or the far end (observation section 12) of the image guide 13 may withdraw within the catheter 1 or the far end (observation section 12) of the image guide 13 may be located at the same position as the far end with respect to the horizontal direction of the catheter 1. For example, when the far end (observation section 12) of the image guide 13 protrudes from the far end of the catheter 1, it is possible to take images forward without the field of view being obstructed, which is advantageous.

The angioscope of the present invention may further include diagnostic or therapeutic means. The diagnostic or therapeutic means refers to means for mechanically processing the interior of blood vessel and may be, for example, directional atherectomy (DCA) apparatus, thrombus aspirator, rotablator or the like. The directional atherectomy is a therapy for recovering a blood flow by inserting a special ultrasmall plane or file into the blood vessel and shaving a pultaceous substance such as atheroma accumulated in the blood vessel using a plane and removing it out of the body. Thrombus suction is a therapy that suctions and removes thrombus produced in the blood vessel. The rotablator has a rapidly spinning tip which shaves arterial sclerosis tissue just like a file. This tip is designed to shave only a hard lesioned part without damaging a normal blood vessel wall. As opposed to many methods including balloon expansion which have no effect on hard lesions involving calcification, the rotablator is characterized in that it is also effective for highly calcified lesions.

As described above, the apparatus of the present invention repeats irradiation of high-intensity pulsed light into the blood vessel, generation of water-vapor bubbles and pulsed illumination at short intervals, and can thereby obtain images of the interior of a blood vessel as moving images. At this time, it is possible to discover a lesioned part in the blood vessel while observing an image and conduct intravascular diagnostics or therapy using the diagnostic or therapeutic means or apparatus.

The directional atherectomy includes a small plane or file, guide wire that communicates them with an operation section and the operation section. The small plane or file is provided at the far end part of the catheter-shaped endoscope of the present invention, the guide wire is passed into the catheter, the guide wire is used to communicate the small plane or file with the operation section outside and the operation section is operated to shave atheroma of arterial sclerosis or thrombus using the small plane or file. The small plane or file is housed in a housing located at the far end part, a window is formed in the housing and arterial sclerosis tissue or the like is removed by pressing the window against the arterial sclerosis tissue and by moving the small plane or file forward. As described above, it is possible to capture images of the intravascular lumen using the endoscope of the present invention, discover an arterial sclerosis region and remove the region using the directional atherectomy apparatus.

The thrombus aspirator is constructed of an aspirator and a suction pump, and the aspirator is provided in the catheter of the catheter-shaped endoscope of the present invention, one end of which communicates with the pump. As described above, it is possible to capture images of the intravascular lumen using the endoscope of the present invention, discover a region where thrombus is generated and suction and remove the thrombus using the thrombus aspirator.

Furthermore, the rotablator includes a rotablator part, a guide wire that communicates the rotablator part with an operation section and the operation section. The rotablator is provided at the far end part of the catheter-shaped endoscope of the present invention, the guide wire is passed into the catheter, the guide wire is used to communicate the rotablator with the operation section outside, the operation section is operated to shave arterial sclerosis atheroma or thrombus using the rotablator. The rotablator especially rotates a file with artificial diamond over ten thousand times per minute, and therefore it can be used to cure even hardened organized thrombus. As described above, it is possible to capture images of the intravascular lumen using the endoscope of the present invention, discover an arterial sclerosis region or thrombus and remove the region using the rotablator.

Furthermore, examples of the means for diagnostics include an apparatus for biopsy. The apparatus for biopsy is constructed of a needle section, guide wire and operation section, and the needle section and operation section communicate with each other through the guide wire, the operation section is operated so as to cause the needle section to collect tissue. The needle section is provided at a far end of the apparatus of the present invention and operated by the operation section through the guide wire as explained above. This apparatus is an apparatus for diagnostics in the sense that it collects part of tissue for biopsy, while it is also an apparatus for therapy because the needle section can also remove a lesioned part. As shown above, it is possible to capture images of the intravascular lumen using the endoscope of the present invention, discover a lesioned region and remove the region using the apparatus for biopsy.

The present invention also includes a method for diagnostics or therapy of an intravascular lumen using an intravascular diagnostic or therapeutic apparatus provided with high-intensity pulsed light generating means and high-intensity pulsed light transmitting means for transmitting high-intensity pulsed light, capable of irradiating the interior of a blood vessel with high-intensity pulsed light, generating water-vapor bubbles and temporarily removing blood in the blood vessel and irradiating the light for intravascular diagnostics or therapy. Examples of this include a method of viewing an intravascular lumen using an angioscope provided with high-intensity pulsed light generating means and high-intensity pulsed light transmitting means for transmitting high-intensity pulsed light, capable of irradiating the interior of a blood vessel with high-intensity pulsed light, generating water-vapor bubbles and temporarily removing blood in the blood vessel, including the steps of irradiating the interior of the blood vessel with high-intensity pulsed light, generating water-vapor bubbles in the blood vessel and temporarily removing blood and irradiating visible light.

Furthermore, the present invention also includes an intra-pipe observation or repair apparatus provided with high-intensity pulsed light generating means and high-intensity pulsed light transmitting means for transmitting high-intensity pulsed light, capable of irradiating the interior of a pipe containing a fluid with high-intensity pulsed light, generating water-vapor bubbles and temporarily removing the fluid in the pipe. The intra-pipe observation or repair apparatus includes pulsed light irradiating means for irradiating light for observation or repair and allowing observation or repair in an intra-pipe wall or intra-pipe joint. For example, the intra-pipe observation or repair apparatus includes illumination light irradiating means for pulsed-illuminating the interior of the pipe and allowing optical observation and image-pickup means for taking images of the intra-pipe wall illuminated with illumination light. The pipe containing the fluid suitable for the use of the apparatus is a pipe that contains a fluid or liquid which shields light used to observe or repair the interior of the pipe to be observed or repaired. Examples of such a fluid or liquid include a fluid or liquid which contains light absorbers or scatterers making passage of light difficult or more specifically a solvent such as toluene, mineral oil such as petroleum, milk, drinking water such as carbonated drink and nontransparent drainage or the like. The inner diameter of the pipe suitable for observation or repair by the apparatus ranges from several mm to over ten mm. The pipe having such a degree of diameter can generate water-vapor bubbles without generating large sound pressure waves.

Examples of the pipe to which the present apparatus is applicable include pipes used for chemical engineering, food engineering manufacturing plant or sewage disposal plant containing the above described solvent, mineral oil, milk, carbonated drink, nontransparent drainage or the like. The material for the pipe in this case is not limited, either and any material such as metal, rubber, synthetic resin such as silicon resin can be targets for observation or repair using the apparatus of the present invention if it can be at least used as the material for pipes in the above described industrial fields.

The high-intensity pulsed light irradiation method is similar to the method for the intravascular diagnostic or therapeutic apparatus provided with high-intensity pulsed light generating means and high-intensity pulsed light transmitting means for transmitting high-intensity pulsed light, capable of irradiating the interior of a blood vessel with high-intensity pulsed light, generating water-vapor bubbles and temporarily removing blood in the blood vessel, and the method for irradiating light for observation or repair and irradiation timing are also similar to those of the intravascular diagnostic or therapeutic apparatus provided with high-intensity pulsed light generating means and high-intensity pulsed light transmitting means for transmitting high-intensity pulsed light, capable of irradiating the interior of a blood vessel with high-intensity pulsed light, generating water-vapor bubbles and temporarily removing blood in the blood vessel. As the light for observation, visible light is used and as light for repair, for example, laser light, ultraviolet light, visible light, infrared light or near-infrared light is used.

Examples of specific use include discovery or repair of damages in a pipe, discovery or removal of foreign matters in the pipe or the like. The "repair" by the apparatus refers to restoring the interior of the pipe to its normal condition and also includes removal of foreign matters. For example, in the above described food engineering plant, microbial contamination inside a liquid-feeding pipe for a drinking fluid may become controversial. In such a case, the use of the apparatus of the present invention makes it possible to discover a microbial colony formed in the pipe and further annihilate the microbes using light for repair. For example, it is possible to annihilate microbes through irradiation of ultraviolet light and also thermally annihilate microbes through irradiation of infrared light.

The present invention will be explained more specifically based on examples below. However, the present invention will not be limited by these examples.

Example 1

Figure 5:
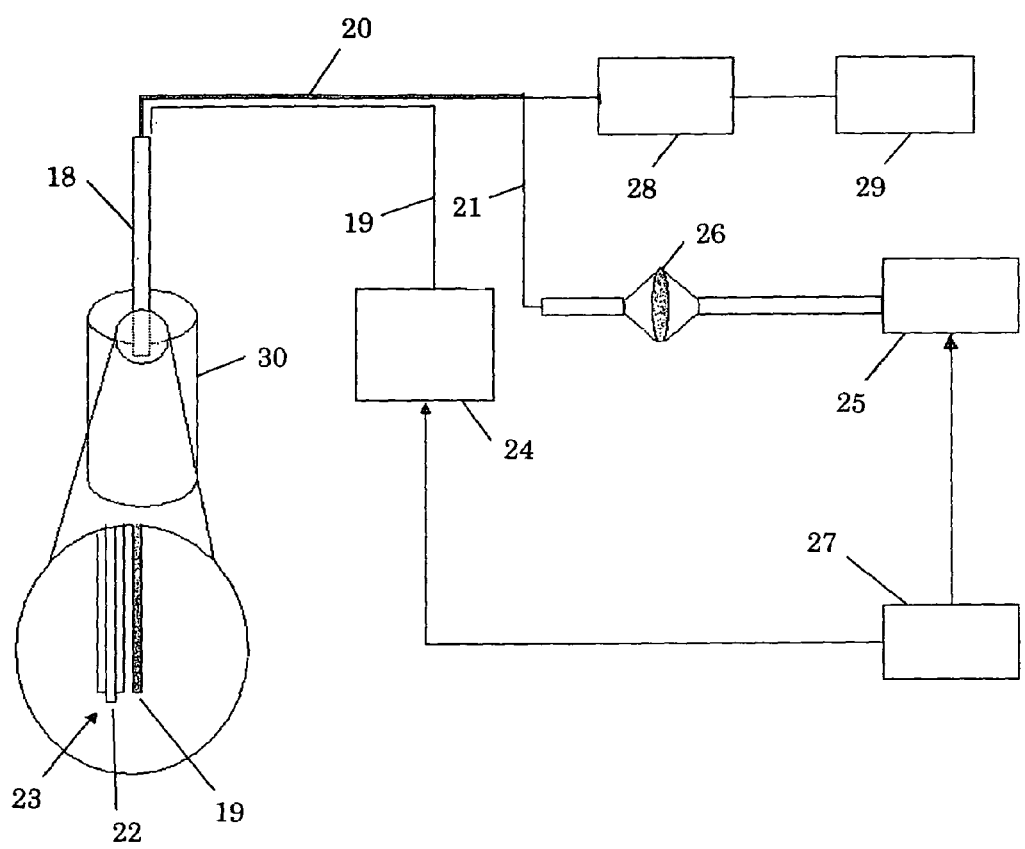
FIG. 5 illustrates an apparatus used in an example.

The endoscope used in this example is shown in FIG. 5. As shown in FIG. 5, a small-diameter endoscope 22 was installed in a stainless steel sheath 23 having a length of approximately 3 cm and an inner diameter of 0.8 cm.

An image guide 20 and a lightguide 21 were placed in the small-diameter endoscope 22. A laser transmission fiber 19 is disposed along those guides and these were placed in a catheter sheath 18. In this case, the small-diameter endoscope 22, that is, the far ends of the image guide 20 and lightguide 21 were made to slightly protrude from the laser transmission fiber 19. Identical quartz optical fibers were used as the optical fibers for image pickup in the laser transmission optical fiber 19 and image guide 20. A plastic lightguide was used for the lightguide 21. The diameter of the laser transmission fiber 19 was approximately 0.6 mm and the diameter of the small-diameter endoscope 22 integrating the lightguide 21 and image guide 20 was approximately 0.7 mm. The laser transmission optical fiber 19 was connected to an Ho:YAG laser generator 24 (LASER1-2-3 SCHWARTZ (ELECTRO-OPTICS (U.S.A.))). Several fibers were used as the optical fiber for transmission of pulsed illumination light of the lightguide 21 for pulsed light illumination. The optical fiber for transmission of pulse illumination light was connected to a flash lamp 25 (fiber video flash MODEL FA-1J10TS (NISSIN ELECTRONIC CO., LTD.)) through a condenser lens 26. In FIG. 5, thick white lines on both sides of the condenser lens 26 denote light. The above described Ho:YAG laser generator 24 and flash lamp 25 were connected via a delay generator 27 (digital display generator BNC555 Series (Seki Technotron Corp.)). A Celfoc lens was disposed at a far end of the optical fiber of the image guide 20 and the opposite end thereof was connected to a CCD camera 28 (endoscope 3CCD video camera system MV-5010A (manufactured by Machida Endoscope Co., Ltd.)). Furthermore, the CCD camera 28 was connected to a monitor 29 (PVM-9040 (manufactured by SONY)) via an RGB cable so as to allow the monitor 29 to observe an image of an intravascular lumen.

The extract porcine coronary artery and porcine blood vessel used in this example were purchased from the Metropolitan Central Wholesale Market Meat Market. The porcine coronary artery 30 was cut into pieces of approximately 5 cm. An end of the porcine coronary artery 30 was ligated, porcine blood with saline or heparin added was put therein, the far end part of the catheter sheath 18 in which the above described laser transmission optical fiber 19, lightguide 21 and image guide 20 were disposed was put in the saline or porcine blood, illuminated with pulse illumination light having a pulse width of 10 μs without irradiating any laser, and images of the intravascular lumen taken by the CCD camera 28 were displayed on the monitor 29 and recorded by a video. Furthermore, the porcine blood was irradiated with laser to produce water-vapor bubbles and images thereof were taken. The intensity of the laser at this time was approximately 200 mJ/pulse and pulse width was approximately 200 μs. The images of the intravascular lumen delayed by the delay generator and obtained by the CCD camera were displayed on a monitor and recorded by a video.

Figure 8:
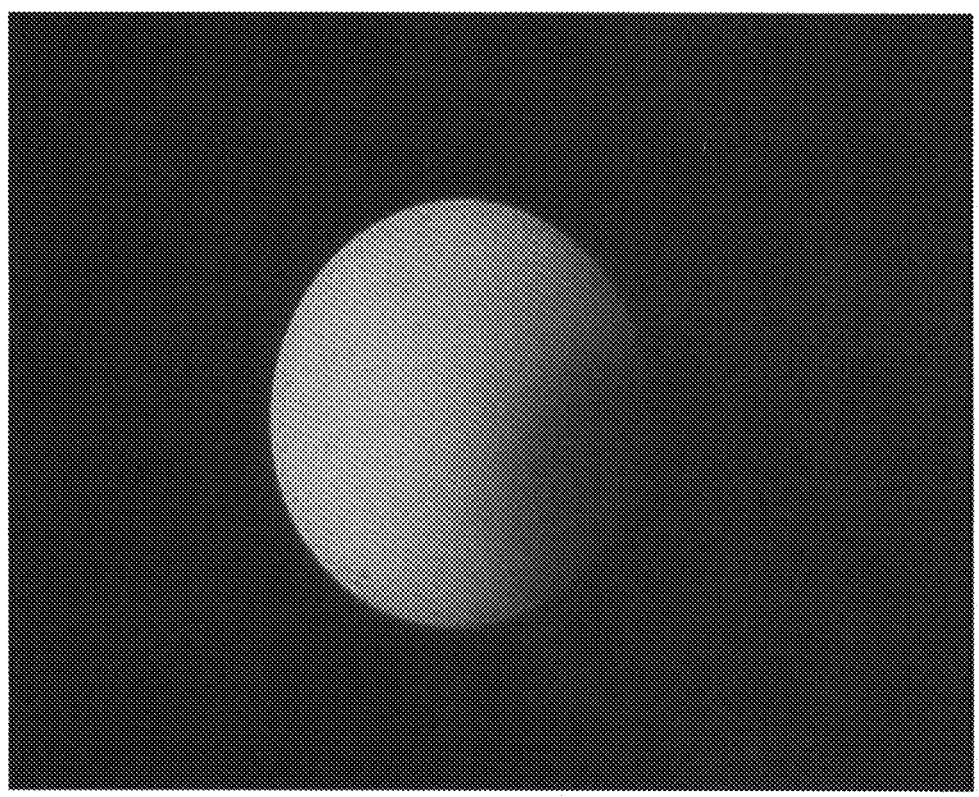
FIG. 8 is a photo of an intravascular lumen when saline is injected into a porcine coronary artery.
Figure 9:
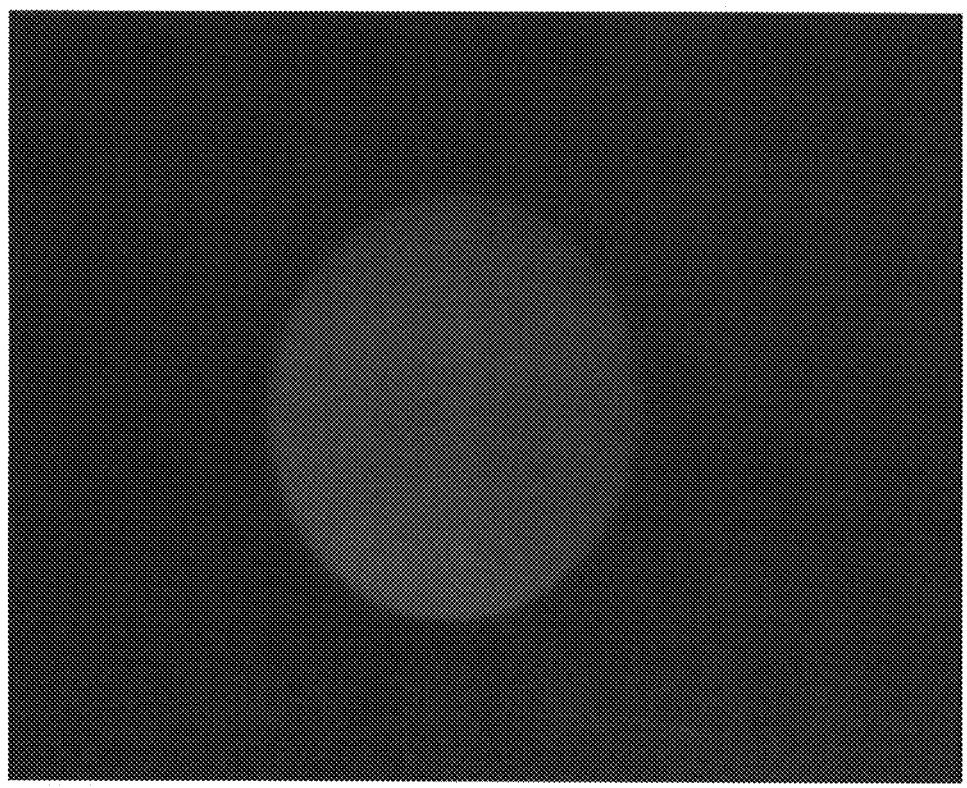
FIG. 9 is a photo of an intravascular lumen when blood of a pig is injected into a porcine coronary artery.
Figure 10:
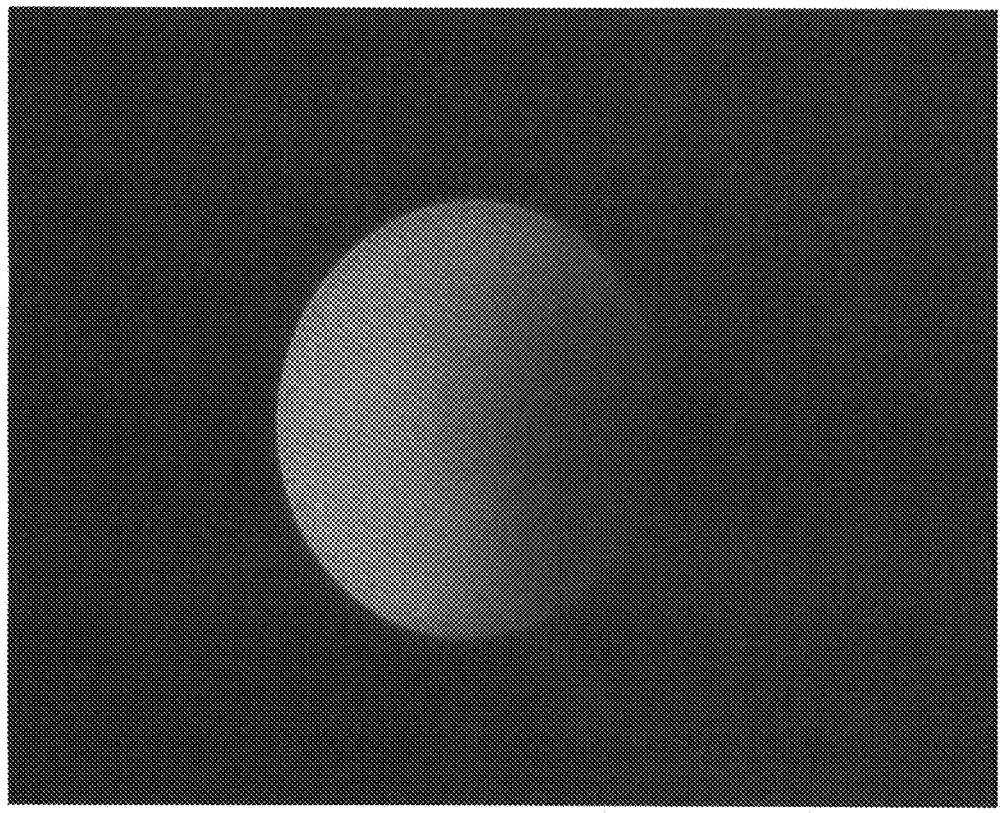
FIG. 10 is a photo of intravascular lumen when blood of a pig is injected into a porcine coronary artery and a pulsed laser is irradiated.

FIG. 8 shows a photo of the intravascular lumen when saline is injected in the porcine coronary artery, FIG. 9 shows a photo of the intravascular lumen when the porcine blood is injected in the porcine coronary artery and FIG. 10 shows a photo of the intravascular lumen when the porcine blood is injected in the porcine coronary artery and pulsed laser is irradiated. As shown in FIG. 9, when an image of the porcine coronary artery was taken with the porcine blood put therein without laser irradiation, the presence of the blood caused the entire image to become red and it was not possible to see the intravascular lumen. On the other hand, as shown in FIG. 9, when transparent saline was put in the porcine coronary artery, it was possible to observe the intravascular lumen. Furthermore, as shown in FIG. 10, when the blood was put and laser was irradiated to generate water-vapor bubbles, the blood in front of the catheter was temporarily removed and therefore it was possible to observe the intravascular lumen. The experiment with saline imitated an endoscope test with a fluid injected according to a conventional method and it was proven that the angioscope using high-intensity pulsed light induced bubbles can obtain images of the intravascular lumen in the same way as in a conventional endoscope test which performs observation with a fluid injected.

Example 2

A silicon tube was filled with milk and the inner wall of the tube was observed using the endoscope of the present invention. The endoscope used was the same as that of Example 1. A silicon tube having an inner diameter of 3 mm was cut open, a piece of paper colored with water-resistant red ink was pasted inside and the silicon tube was closed again. Next, a far end part of a catheter sheath 18 in which a laser transmission optical fiber 19 of the endoscope, lightguide 21 and image guide 20 were disposed was inserted into the silicon tube and the tube was put in the milk so that the tube was filled with the milk. Next, pulsed laser was irradiated to generate water-vapor bubbles and images thereof were taken. The laser intensity at this time was 200 mJ/pulse or 450 mJ/pulse at the end of the laser irradiation fiber. The pulse width was approximately 200 μs. The images of the intravascular lumen delayed by a delay generator and taken by a CCD camera were displayed on a monitor and recorded by a video. The delay time was 70 μs or 140 μs when the laser intensity was 200 mJ/pulse and 70 μs, 105 μs, 140 μs, 175 μs and 210 μs when the laser intensity was 450 mJ/pulse. As the control at this time, the images were taken without irradiating any laser. Moreover, images of the tube without being filled with milk but filled with air were likewise taken and they were left under control in the air. When the laser intensity was 450 mJ/pulse, the size and brightness of images of the interior of the silicon tube (parts that look bright) taken with various delay times were measured and expressed as relative values with the value with a delay time 70 μs assumed to be 1. The size of the image increased when a scattering liquid (milk) was located before a focus position because the image became out of focus, while the size of the image decreased when the scattering liquid (milk) was removed to a place away from the focus position because focus was achieved. Furthermore, the brightness of the screen indicates the extent to which the scattering liquid (milk) existed in the field of view of observation (part that can be observed with illumination light) and the fact of getting dark indicates that the scattering liquid in the field of view of observation has been removed. The images obtained were expressed using color processing software (Photoshop (Adobe Systems, Inc., U.S.A.) with an L*a*b* display system and the sizes of the images were obtained by measuring the radii of parts of Lab images whose brightness was 20 or greater using calipers and the brightness was obtained by measuring the brightest part of the Lab images.

Figure 11:
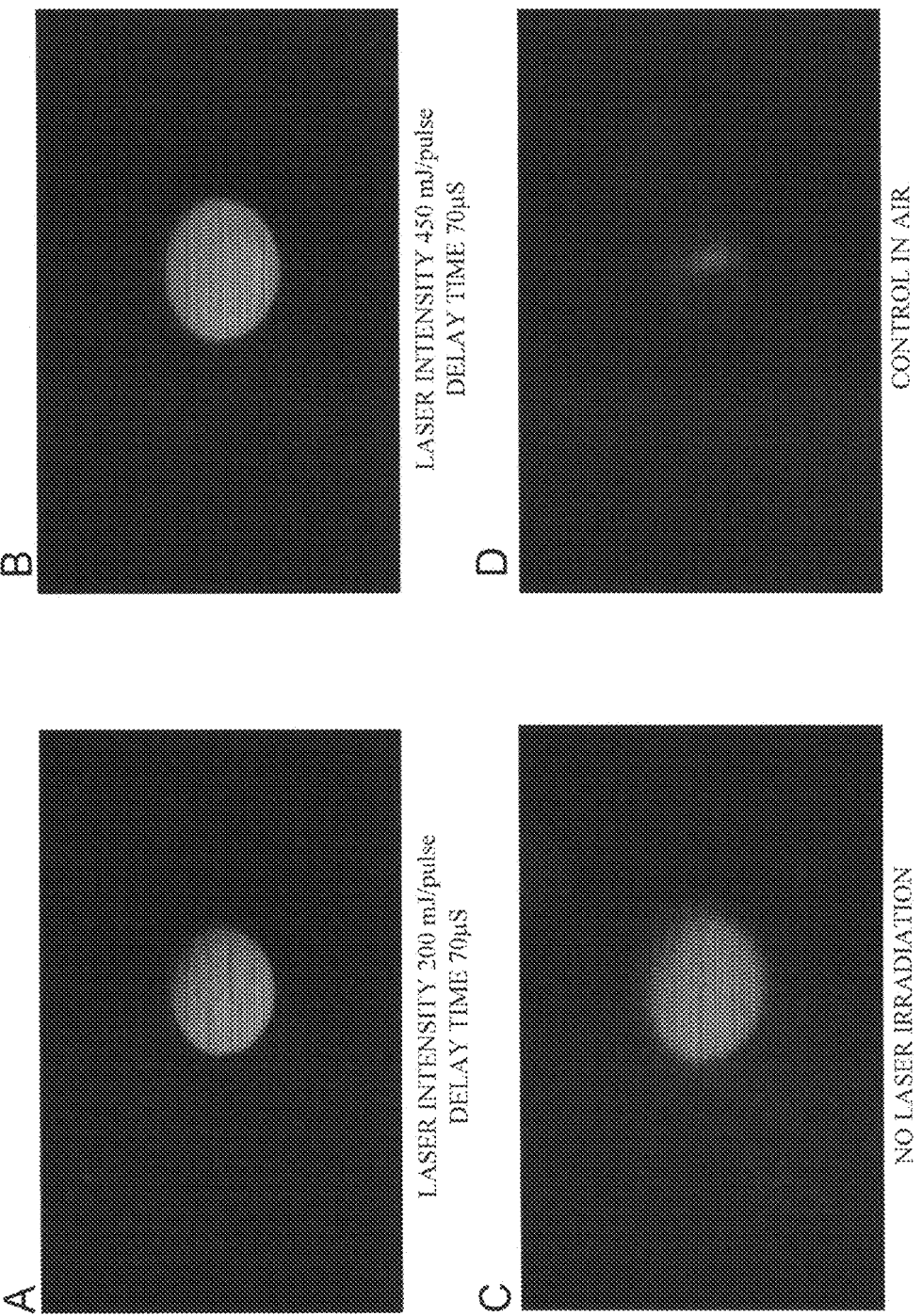
FIG. 11 shows photos when a silicon tube is filled with milk and the interior of the tube is observed with a delay time 70 μs.

The results are shown in FIG. 11 and FIG. 12. FIG. 11 shows the image pickup results with a delay time of 70 μs (0.05 deg); FIG. 11A with laser intensity of 200 mJ/pulse (charging voltage 900 V), FIG. 11B with laser intensity of 450 mJ/pulse (charging voltage 1000 V), FIG. 11C without laser irradiation (control) and FIG. 11D under control in the air. FIG. 12 shows the image pickup results with a delay time of 140 μs (0.1 deg); FIG. 12A with laser intensity of 200 mJ/pulse (charging voltage 900 V), FIG. 12B with laser intensity of 450 mJ/pulse (charging voltage 1000 V), FIG. 12C without laser irradiation (control) and FIG. 12D under control in the air. When no water-vapor bubbles are generated, milk exists in the vicinity of the illumination section and observation section, and therefore illumination light emitted from the illumination section is diffused and reflected by milk and their images glow white and also have high brightness. On the other hand, when small water-vapor bubbles are generated, images of red paper inside the silicon tube are taken, and so they look red and also have low brightness. Furthermore, when appropriate water-vapor bubbles in sufficient sizes are generated, milk in the vicinity of the illumination section and observation section is removed, there is no more diffusion or reflection with milk and nothing appears in images (same as control in the air). That is, the condition under which nothing appears is the best condition.

Figure 13:
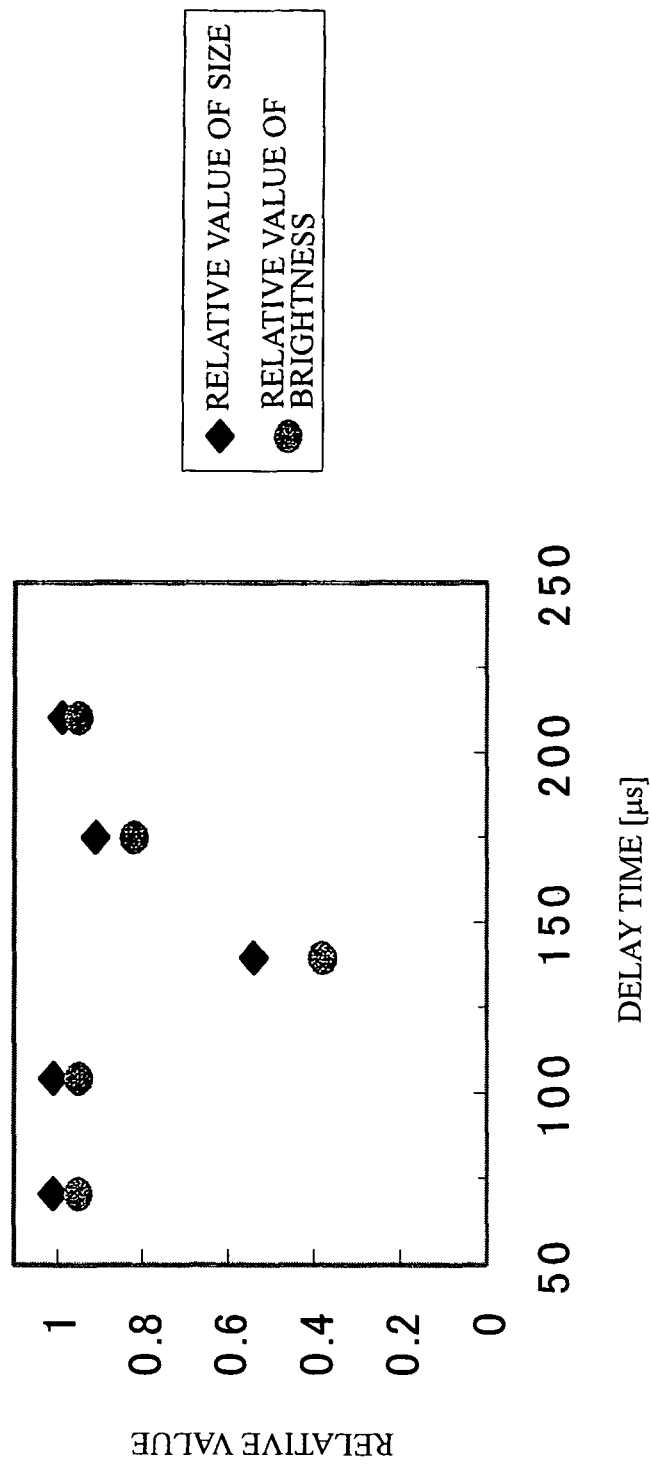
FIG. 13 illustrates a relation between a delay time between laser irradiation and pulsed illumination, and size of the image taken and relative intensity of brightness, when a silicon tube is filled with milk, irradiated with a laser and images of the interior of the tube are taken.

FIG. 13 shows relative values of sizes and relative values of brightness corresponding to various delay times when laser intensity is 450 mJ/pulse. When both the size and brightness of an image are small, this means that water-vapor bubbles of sufficient sizes have been generated.

In both FIG. 11 and FIG. 12, no water-vapor bubbles are generated under control (with no laser irradiation), and therefore the images look white. When the delay time is 70 μs and when laser intensity is 200 mJ/pulse, generation of water-vapor bubbles is insufficient, and therefore the image of milk looks white and when laser intensity is 450 mJ/pulse, images are taken before water-vapor bubbles grow big enough, and therefore images look red (FIG. 11). Both when the delay time is 140 μs and when laser intensity is 200 mJ/pulse and 450 mJ/pulse, images are taken when water-vapor bubbles have grown big enough, and therefore nothing appears as in the case of control in the air (FIG. 12). Furthermore, when laser intensity is 450 mJ/pulse, if the delay time is set to 70 μs to 210 μs, both the size and brightness of the image of the interior of the tube were a minimum when the delay time was 140 μs (FIG. 13). From the experiment conducted in Example 2, the best field of view was obtained with the delay time 140 μs.

Example 3

An aorta lumen of Japanese white rabbit was observed using the endoscope of the present invention. The structure of the endoscope used is in conformance with the endoscope shown in FIG. 5 used in Example 1, but a flash lamp excitation Ho:YAG laser (manufactured by Cyber Laser, model FLHY-1) was used for the laser generator. Furthermore, a fiber having a core diameter of 0.6 mm, outside diameter of 1.45 mm was used as the laser irradiation fiber and this fiber was used tied with an endoscope having an outside diameter of 1.3 mm (manufactured by au Medical Laboratory).

A 10 Fr. sheath was held to Japanese white rabbit aorta and the above described fiber tied with the endoscope was inserted therein.

The laser irradiation condition was 10 Hz, 400 mJ/pulse. As the control, images of the intravascular lumen were taken without laser irradiation.

Figure 14:
FIG. 14 shows a photo when an aorta lumen of Japanese white rabbit is observed without laser irradiation using the apparatus of the present invention.
Figure 15:
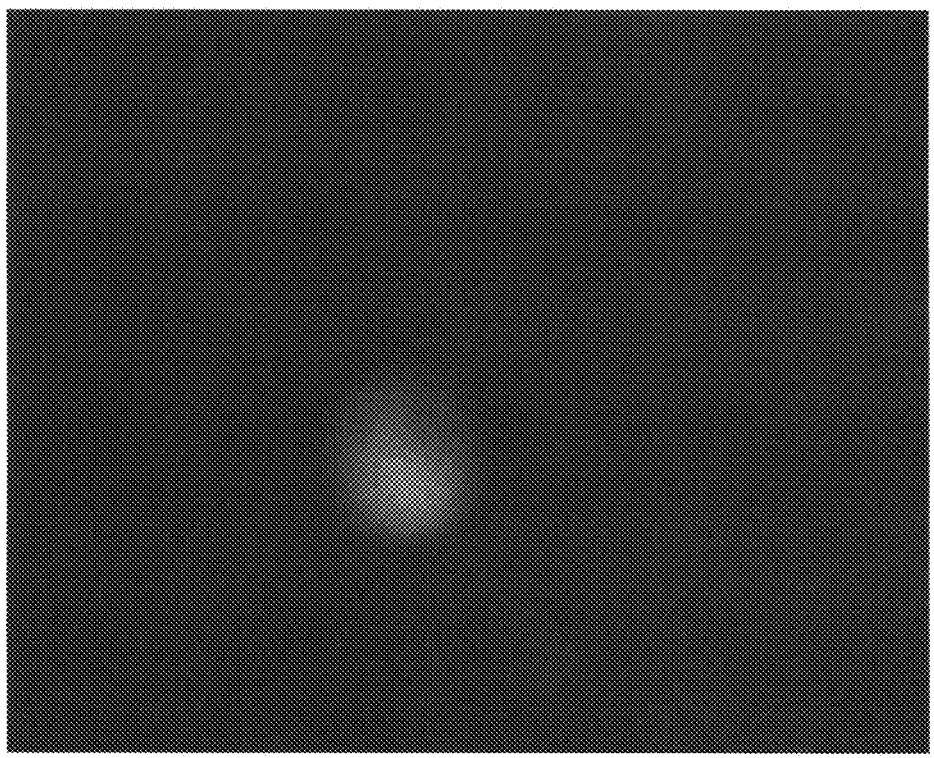
FIG. 15 shows a photo when an aorta lumen of Japanese white rabbit is observed through laser irradiation using the apparatus of the present invention.

FIG. 14 shows a photo of the intravascular lumen taken without laser irradiation and FIG. 15 shows a photo of the intravascular lumen irradiated with laser and with water-vapor bubbles generated. When an image was taken without laser irradiation, blood existed and so the entire image looked red and it was not possible to see the intravascular lumen. When the laser was irradiated to generate water-vapor bubbles, blood in the blood vessel in front of the sheath was temporarily removed, and therefore it was possible to observe the intravascular lumen.

The entire disclosure of the publications, patents and patent applications quoted in the present specification is incorporated herein by reference in its entirety.

INDUSTRIAL APPLICABILITY

As shown in the examples, by irradiating the interior of a pipe containing a liquid with high-intensity pulsed light, water-vapor bubbles are generated and the liquid is temporarily removed. By irradiating the interior of a blood vessel with high-intensity pulsed light, water-vapor bubbles are generated in blood in an intravascular lumen and the blood in that part is temporarily removed, and therefore it is possible to optically observe the intravascular lumen without being influenced by the blood or without using ultrasound or the like. The examples irradiated visible light to enable optical observation as light for diagnostics or therapy, obtained the reflected image to enable optical observation of the intravascular lumen, and it is possible to realize various types of diagnostics or therapy by changing the wavelength of light. Furthermore, Example 3 actually observed the intravascular lumen of a living animal. The present invention does not involve blood obstruction or injection of a large volume of heterogeneous solution, does not require stoppage of blood, which is an oxygen carrier, and can secure a supply of oxygen to peripherals, and therefore it is minimally invasive and capable of conducting diagnostics or therapy of a coronary artery or the like easily and safely, which has been difficult using a highly invasive conventional apparatus.

Furthermore, as shown in Example 2, the apparatus of the present invention can conduct not only intravascular diagnostics or therapy but also observation or repair of an artificial tubular object.

The apparatus of the present invention can be used for diagnostics or therapy of an intravascular lumen. The apparatus of the present invention can conduct diagnostics or therapy of the intravascular lumen without stopping any blood flow in the blood vessel as with a conventional intravascular diagnostic or therapeutic apparatus, and can thereby be used as a minimally invasive intravascular lumen diagnostic or therapeutic apparatus.

The invention claimed is:

1. An intravascular apparatus for obtaining visible images of an interior of a blood vessel, comprising:
   (A) a catheter configured to be inserted into the blood vessel, the catheter comprising:
      (i) a first light transmitting fiber that includes a first light irradiation section and that is connected to a first light source, which generates a pulsed first light and which transmits the pulsed first light via the first light transmitting fiber to the first light irradiation section, wherein the pulsed first light irradiates into the blood vessel to generate bubbles within the blood vessel;
      (ii) a second light transmitting fiber that includes a second irradiation section and that is connected to a second light source, which generates a visible second light and which transmits the visible second light via the second light transmitting fiber to the second light irradiation section, wherein the visible second light irradiates into the blood vessel to illuminate the interior of the blood vessel to enable optical observation during generation of the bubbles; and
      (iii) an image guide that includes an observation section and is connected to an imaging device configured to obtain images of the interior of the blood vessel; and
   (B) a delay generator, connected to the first light source and the second light source, that is configured to receive a signal from an electrocardiograph or a pressure sensor, wherein said signal correlates with pulsating blood flow within the blood vessel, such that, when the pulsating blood flow decreases, the delay generator (a) triggers the first light source to irradiate the pulsed first light and (b) triggers the second light source to irradiate the visible second light several tens of µs to several hundreds of µs after the first light source is triggered.

2. The intravascular apparatus for obtaining visible images of the interior of the blood vessel according to claim 1, wherein the catheter further includes a liquid feeding channel, wherein the liquid feeding channel includes an injection port and is connected to a liquid reservoir, and wherein the liquid feeding channel replaces blood in a local region irradiated with the pulsed first light with a liquid whose absorbability of the pulsed first light is close to that of water.

3. The intravascular apparatus for obtaining visible images of the interior of the blood vessel according to claim 1, wherein the visible second light comprises an ultraviolet light having a wavelength less than or equal to 400 nm so that the blood vessel relaxes.

4. The intravascular apparatus for obtaining visible images of the interior of the blood vessel according to claim 1, wherein the visible second light comprises a visible light having a wavelength around 458 nm or 514.5 nm or infrared light having a wavelength greater than or equal to 800 nm so that the blood vessel contracts.

5. The intravascular apparatus for obtaining visible images of the interior of the blood vessel according to claim 1, wherein the visible second light comprises high intensity light.

6. The intravascular apparatus for obtaining visible images of the interior of the blood vessel according to claim 1, wherein the visible second light comprises a free electron laser having a wavelength of about 5.75 µm so that atheroma of arterial sclerosis in the blood vessel or thrombus in the blood vessel is destroyed.

7. The intravascular apparatus for obtaining visible images of the interior of the blood vessel according to claim 1, wherein the second light source is selected from a group consisting of light generated by a solid laser, semiconductor laser, dye laser, variable wavelength near-infrared laser, optical parametric oscillator (OPO), Raman laser, and a non-linear optical converter and flash lamp.

8. The intravascular apparatus for obtaining visible images of the interior of the blood vessel according to claim 1, wherein the pulsed first light is generated by an optical parametric oscillator (OPO).

9. The intravascular apparatus for obtaining visible images of the interior of the blood vessel according to claim 1, wherein the first light source comprises a laser, wherein the laser is a solid laser using rare-earth ions.

10. The intravascular apparatus for obtaining visible images of the interior of the blood vessel according to claim 9, wherein a laser medium is Ho or Tm and a laser base material is selected from a group of YAG, YLF, YSGG and YVO.

11. The intravascular apparatus for obtaining visible images of the interior of the blood vessel according to claim 10, wherein the laser is Ho:YAG laser or Tm:YAG laser.

12. The intravascular apparatus for obtaining visible images of the interior of the blood vessel according to claim 1, which further comprises a diagnostic or therapeutic apparatus configured to mechanically process the interior of the blood vessel.

13. The intravascular apparatus for obtaining visible images of the interior of the blood vessel according to claim 12, wherein the diagnostic or therapeutic apparatus is selected from a group consisting of a directional atherectomy apparatus, thrombus aspirator, rotablator and apparatus for biopsy.

14. The intravascular apparatus for obtaining visible images of the interior of the blood vessel according to claim 1, wherein the wavelength of the pulsed first light ranges from 1.5 µm to 3 µm.

15. The intravascular apparatus for obtaining visible images of the interior of the blood vessel according to claim 1, wherein the wavelength of the pulsed first light ranges from 1.5 µm to 2.5 µm.

16. The intravascular apparatus for obtaining visible images of the interior of the blood vessel according to claim 1, wherein the wavelength of the pulsed first light is 1.9 µm.

17. The intravascular apparatus for obtaining visible images of the interior of the blood vessel according to claim 1, wherein the pulse width of the pulsed first light ranges from 100 µs to 1 ms.

18. The intravascular apparatus for obtaining visible images of the interior of the blood vessel according to claim 1, wherein the pulse width of the pulsed first light ranges from 150 µs to 250 µs.

19. The intravascular apparatus for obtaining visible images of the interior of the blood vessel according to claim 1, wherein the first light irradiation section protrudes from the catheter.

20. The intravascular apparatus for obtaining visible images of the interior of the blood vessel according to claim 1, wherein the catheter further includes a pressure sensor connected to the first light source.

21. The intravascular apparatus for obtaining visible images of the interior of the blood vessel according to claim 1, further comprising an electrocardiogram connected to the delay generator and the first light source.

22. The intravascular apparatus for obtaining visible images of the interior of the blood vessel according to claim 1, wherein the pulsed first light has a wavelength that ranges from 0.3 µm to 3 µm and a pulse width that ranges from 10 ns to 10 ms.

23. A method for obtaining visible images of an interior of a blood vessel, comprising:
  (A) inserting a catheter into the blood vessel of a subject, the catheter comprising:
    (i) a first light transmitting fiber that includes a first light irradiation section and that is connected to a first light source, which generates a pulsed first light and which transmits the pulsed first light via a first light transmitting fiber to the first light irradiation section, wherein the pulsed first light irradiates into the blood vessel to generate bubbles within the blood vessel;
    (ii) a second light transmitting fiber that includes a second irradiation section and that is connected to a second light source, which generates a visible second light and which transmits the visible second light via the second light transmitting fiber to the second light irradiation section, wherein the visible second light irradiates into the blood vessel to illuminate the interior of the blood vessel to enable optical observation during generation of the bubbles; and
    (iii) an image guide that includes an observation section and is connected to an imaging device configured to obtain images of the interior of the blood vessel, wherein the first light source and the second light source are connected to a delay generator; and then
  (B) irradiating the pulsed first light into the blood vessel to generate bubbles when pulsating blood flow within the blood vessel decreases;
  (C) irradiating the visible second light with delay between the irradiation of the visible second light and the pulsed first light such that the visible second light is irradiated several tens of µs to several hundreds of µs after step (B) occurs; and
  (D) obtaining the images of the interior of the blood vessel.

24. The method according to claim 23, wherein the first light source is connected to a pressure sensor, and wherein step (B) occurs when a pulsating blood flow monitored by the pressure sensor decreases.

25. The method according to claim 23, wherein the delay generator is connected to an electrocardiogram, and wherein step (B) occurs when a pulsating blood flow monitored by the electrocardiogram decreases.

26. The method according to claim 23, further comprising feeding liquid, whose absorbability of the pulsed first light is close to that of water, into the blood vessel before step (C) to replace blood in a local region irradiated with the pulsed light with the liquid, wherein the catheter further includes a liquid feeding channel which includes an injection port and is connected to a liquid reservoir.

27. The method according to claim 23, wherein the visible second light comprises an ultraviolet light having a wavelength less than or equal to 400 nm and the irradiation of the visible second light relaxes the blood vessel.

28. The method according to claim 23, wherein the visible second light comprises a visible light having a wavelength around 458 nm or 514.5 nm or infrared light having a wavelength greater than or equal to 800 nm and the irradiation of the visible second light contracts the blood vessel.

29. The method according to claim 23, wherein the visible second light comprises high intensity light.

30. The method according to claim 23, wherein the visible second light comprises a free electron laser having a wavelength of about 5.75 µm and destroying atheroma of arterial sclerosis in the blood vessel or thrombus in the blood vessel.

31. The method according to claim 23, wherein the second light source is selected from a group consisting of light generated by a solid laser, semiconductor laser, dye laser, variable wavelength near-infrared laser, optical parametric oscillator (OPO), Raman laser, and a non-linear optical converted and flash lamp.

32. The method according to claim 23, wherein the pulsed first light is generated by an optical parametric oscillator (OPO).

33. The method according to claim 23, wherein the first light source comprises a laser, wherein the laser is a solid laser using rare-earth ions.

34. The method according to claim 23, wherein a laser medium is Ho or Tm and a laser base material is selected from a group of YAG, YLF, YSGG and YVO.

35. The method according to claim 23, wherein the laser is a Ho:YAG laser or a Tm:YAG laser.

36. The method according to claim 23, further comprising conducting diagnostic or therapy.

37. The method according to claim 36, wherein the therapy is conducted by an apparatus selected from the group consisting of directional atherectomy apparatus, thrombus aspirator, rotablator and apparatus for biopsy.

38. The method according to claim 23, wherein the pulsed first light has a wavelength that ranges from 0.3 μm to 3 μm and a pulse width that ranges from 10 ns to 10 ms.

* * * * *